US012384737B2

(12) United States Patent
Bara et al.

(10) Patent No.: US 12,384,737 B2
(45) Date of Patent: Aug. 12, 2025

(54) COMPOUNDS FOR SOLUBILIZING POLYMERS

(71) Applicant: The Board of Trustees of The University of Alabama, Tuscaloosa, AL (US)

(72) Inventors: Jason Edward Bara, Tuscaloosa, AL (US); Shuai Qian, Northport, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 671 days.

(21) Appl. No.: 17/708,589

(22) Filed: Mar. 30, 2022

(65) Prior Publication Data

US 2022/0411359 A1 Dec. 29, 2022

Related U.S. Application Data

(60) Provisional application No. 63/196,894, filed on Jun. 4, 2021.

(51) Int. Cl.
| | | |
|---|---|---|
| *C08J 11/24* | (2006.01) | |
| *C07C 43/13* | (2006.01) | |
| *C07C 49/167* | (2006.01) | |
| *C07C 49/175* | (2006.01) | |
| *C08J 11/26* | (2006.01) | |

(52) U.S. Cl.
CPC .......... *C07C 49/175* (2013.01); *C07C 43/135* (2013.01); *C07C 49/167* (2013.01); *C08J 11/24* (2013.01); *C08J 11/26* (2013.01)

(58) Field of Classification Search
USPC ...................................................... 521/43.5
See application file for complete search history.

(56) References Cited

U.S. PATENT DOCUMENTS

2010/0032617 A1 2/2010 Gilbeau et al.

OTHER PUBLICATIONS

María Perez-Sanchez et al. Improved synthesis of disaccharides Tetrahedron vol. 67, Issue 40, Oct. 7, 2011, pp. 7708-7712 (Year: 2011).*
Ken-ichi Shimizu et al. The scope and limitation of the regio- and enantioselective hydrolysis of aliphatic epoxides Tetrahedron: Asymmetry vol. 21, Issue 16, Aug. 23, 2010, pp. 2043-2049 (Year: 2010).*
Hoyos et al. Highly Efficient and Sustainable Synthesis of Neoglycoproteins Using Galactosidases; ACS Sustainable Chemistry & Engineering 2020 8 (16), 6282-6292 (Year: 2020).*
Aghaie, M.; Rezaei, N.; Zendehboudi, S., A systematic review on CO2 capture with ionic liquids: Current status and future prospects. Renewable and Sustainable Energy Reviews 2018, 96, 502-525.
Aldea, L.; Fraile, J. M.; García-Marín, H.; García, J. I.; Herrerías, C. I.; Mayoral, J. A.; Pérez, I., Study of the recycling possibilities for azabis(oxazoline)-cobalt complexes as catalysts for enantioselective conjugate reduction. Green Chemistry 2010, 12 (3), 435-440.
Aldea, L.; García, J. I.; Mayoral, J. A., Multiphase enantioselective Kharasch—Sosnovsky allylic oxidation based on neoteric solvents and copper complexes of ditopic ligands. Dalton Transactions 2012, 41 (27), 8285-8289.
Amaral, M.; Crespo, E. A.; Dariva, C.; Vega, L. F.; Carvalho, P. J.; Coutinho, J. A. P., High-pressure solubility of CO2 in glymes. Fuel 2018, 219, 120-125.
Ampatzidis, C. D.; Varka, E. M. A.; Karapantsios, T. D., Interfacial activity of amino acid-based glycerol ether surfactants and their performance in stabilizing O/W cosmetic emulsions. Colloids and Surfaces A: Physicochemical and Engineering Aspects 2014, 460, 176-183.
Anastas, P.; Eghbali, N., Green Chemistry: Principles and Practice. Chemical Society Reviews 2010, 39 (1), 301-312.
Ayoub, M.; Abdullah, A. Z., Critical review on the current scenario and significance of crude glycerol resulting from biodiesel industry towards more sustainable renewable energy industry. Renewable and Sustainable Energy Reviews 2012, 16(5), 2671-2686.
Bader, R. F.; Carroll, M. T.; Cheeseman, J. R.; Chang, C., Properties of Atoms in Molecules: Atomic vols. J. Am. Chem. Soc. 1987, 109, 7968-7979.
Bannwarth, C.; Ehlert, S.; Grimme, S., GFN2-xTB—An Accurate and Broadly Parametrized Self-Consistent Tight-Binding Quantum Chemical Method with Multipole Electrostatics and Density-Dependent Dispersion Contributions. J. Chem. Theory Comput. 2019, 15, 1652-1671.
Bara, J. E.; Finotello, A.; Magee, J. W.; Qian, S.; O'Harra, K. E.; Dennis, G. P.; Noble, R. D., 110th Anniversary: Properties of Imidazolium-Based Ionic Liquids Bearing Both Benzylic and n-Alkyl Substituents. Industrial & Engineering Chemistry Research 2019, 58 (38), 17956-17964.
Bayón, C.; Cortés, A.; Aires-Trapote, A.; Civera, C.; Hernáiz, M. J., Highly efficient and regioselective enzymatic synthesis of β-(1→3) galactosides in biosolvents. RSC Advances 2013, 3 (30), 12155-12163.
Becke, A. D., A New Mixing of Hartree-Fock and Local Density-Functional Theories. J. Chem. Phys. 1993, 98, 1372-1377.
Becke, A. D., Density-Functional Exchange-Energy Approximation with Correct Asymptotic Behavior. Phys. Rev. A 1988, 38, 3098.
Boys, S. F.; Bernardi, F., The Calculation of Small Molecular Interactions by the Differences of Separate Total Energies. Some Procedures with Reduced Errors. Mol. Phys. 1970, 19, 553-566.
Brandenburg, J. G.; Bannwarth, C.; Hansen, A.; Grimme, S., B97-3c: A Revised Low-Cost Variant of the B97-D Density Functional Method. J. Chem. Phys. 2018, 148, 064104.

(Continued)

*Primary Examiner* — Terressa Boykin
(74) *Attorney, Agent, or Firm* — Meunier Carlin & Curfman LLC

(57) ABSTRACT

Disclosed are compounds and methods for solubilizing polymers and oligomers. The compounds have the formula:

$$R^1O\diagdown\diagup Q^1\diagdown Q^2,$$

wherein $R^1$, $Q^1$ and $Q^2$ are defined herein.

16 Claims, 3 Drawing Sheets

(56) References Cited

OTHER PUBLICATIONS

Celentano, W.; Neri, G.; Distante, F.; Li, M.; Messa, P.; Chirizzi, C.; Chaabane, L.; De Campo, F.; Metrangolo, P.; Baldelli Bombelli, F.; Cellesi, F., Design of fluorinated hyperbranched polyether copolymers for 19F MRI nanotheranostics. Polymer Chemistry 2020, 11 (24), 3951-3963.

Chen, F.-F.; Huang, K.; Zhou, Y.; Tian, Z.-Q.; Zhu, X.; Tao, D.-J.; Jiang, D.-e.; Dai, S., Multi-Molar Absorption of CO2 by the Activation of Carboxylate Groups in Amino Acid Ionic Liquids. Angewandte Chemie International Edition 2016, 55 (25), 7166-7170.

Finotello, A.; Bara, J. E.; Camper, D.; Noble, R. D., Room-Temperature Ionic Liquids: Temperature Dependence of Gas Solubility Selectivity. Industrial & Engineering Chemistry Research 2008, 47 (10), 3453-3459.

Flowers, B. S.; Mittenthal, M. S.; Jenkins, A. H.; Wallace, D. A.; Whitley, J. W.; Dennis, G. P.; Wang, M.; Turner, C. H.; Emel'yanenko, V. N.; Verevkin, S. P.; Bara, J. E., 1,2,3-Trimethoxypropane: A Glycerol-Derived Physical Solvent for CO2 Absorption. ACS Sustainable Chemistry & Engineering 2017, 5 (1), 911-921.

Frisch, M.; Trucks, G.; Schlegel, H. B.; Scuseria, G. E.; Robb, M. A.; Cheeseman, J. R.; Scalmani, G.; Barone, V.; Mennucci, B.; Petersson, G., et al., Gaussian 09, Revision D. 01, Gaussian. Inc., Wallingford CT 2009.

García, J. I.; García-Marín, H.; Mayoral, J. A.; Pérez, P., Green solvents from glycerol. Synthesis and physico-chemical properties of alkyl glycerol ethers. Green Chemistry 2010, 12 (3), 426-434.

García, J. I.; García-Marín, H.; Mayoral, J. A.; Pérez, P., Quantitative structure-property relationships prediction of some physico-chemical properties of glycerol based solvents. Green Chemistry 2013, 15 (8), 2283-2293.

García-Marín, H.; van der Toorn, J. C.; Mayoral, J. A.; García, J. I.; Arends, I. W. C. E., Epoxidation of cyclooctene and cyclohexene with hydrogen peroxide catalyzed by bis[3,5-bis(trifluoromethyl)-diphenyl] diselenide: Recyclable catalyst-containing phases through the use of glycerol-derived solvents. Journal of Molecular Catalysis A: Chemical 2011, 334 (1), 83-88.

Gatti, M.; Martelli, E.; Marechal, F.; Consonni, S., Review, modeling, Heat Integration, and improved schemes of Rectisol®-based processes for CO2 capture. Applied Thermal Engineering 2014, 70 (2), 1123-1140.

Ghasem, N., Chapter 21—CO2 removal from natural gas. In Advances in Carbon Capture, Rahimpour, M. R.; Farsi, M.; Makarem, M. A., Eds. Woodhead Publishing: 2020; pp. 479-501.

Grimme, S.; Antony, J.; Ehrlich, S.; Krieg, H., A Consistent and Accurate ab initio Parametrization of Density Functional Dispersion Correction (DFT-D) for the 94 Elements H-Pu. J. Chem. Phys. 2010, 132, 154104.

Grimme, S.; Bannwarth, C.; Shushkov, P., A Robust and Accurate Tight-Binding Quantum Chemical Method for Structures, Vibrational Frequencies, and Noncovalent Interactions of Large Molecular Systems Parametrized for All spd-Block Elements (Z = 1-86). J. Chem. Theory Comput. 2017, 13, 1989-2009.

Guseinova, A. T.; Magerramov, A. M.; Allakhverdiev, M. A., [(Polyfluoroalkoxy)methyl]thiiranes and 2-anilinoethanethiols. Russian Journal of Organic Chemistry 2008, 44 (7), 946-949.

Henni, A.; Tontiwachwuthikul, P.; Chakma, A., Solubilities of Carbon Dioxide in Polyethylene Glycol Ethers. The Canadian Journal of Chemical Engineering 2005, 83 (2), 358-361.

Humphrey, W.; Dalke, A.; Schulten, K., VMD: Visual Molecular Dynamics. J. Mol. Graphics 1996, 14, 33-38.

Izgorodina, E. I.; Seeger, Z. L.; Scarborough, D. L. A.; Tan, S. Y. S., Quantum Chemical Methods for the Prediction of Energetic, Physical, and Spectroscopic Properties of Ionic Liquids. Chem. Rev. 2017, 117, 6696-6754.

Izquierdo, J. F.; Montiel, M.; Palés, I.; Outón, P. R.; Galán, M.; Jutglar, L.; Villarrubia, M.; Izquierdo, M.; Hermo, M. P.; Ariza, X., Fuel additives from glycerol etherification with light olefins: State of the art. Renewable and Sustainable Energy Reviews 2012, 16 (9), 6717-6724.

Johnson, E. R.; Keinan, S.; Mori-Sánchez, P.; Contreras-García, J.; Cohen, A. J.; Yang, W., Revealing Noncovalent Interactions. J. Am. Chem. Soc. 2010, 132, 6498-6506.

Karuna, M. S. L.; Devi, B. L. A. P.; Prasad, P. S. S.; Prasad, R. B. N., Synthesis of Sulfated Sodium Salts of 1-Alkylamino-3-alkyloxy-2-propanols and N,N-Di-(2-hydroxy-3-alkyloxy propyl) Alkylamines as Potential Surfactants. Journal of Surfactants and Detergents 2009, 12 (2), 117-123.

Klamt, A., The Cosmo and Cosmo-RS solvation models. Wiley Interdiscip. Rev.: Comput. Mol. Sci. 2011, 1, 699-709.

Klamt, A.; Eckert, F.; Arlt, W., Cosmo-RS: An Alternative to Simulation for Calculating Thermodynamic Properties of Liquid Mixtures. Annu. Rev. Chem. Biomol. Eng. 2010, 1, 101-122.

Leal-Duaso, A.; Favier, I.; Pla, D.; Pires, E.; Gómez, M., Design of Glycerol-Based Solvents for the Immobilization of Palladium Nanocatalysts: A Hydrogenation Study. ACS Sustainable Chemistry & Engineering 2021, 9 (19), 6875-6885.

Leal-Duaso, A.; Gracia-Barberán, S.; Mayoral, J. A.; García, J. I.; Pires, E., Readily Scalable Methodology for the Synthesis of Nonsymmetric Glyceryl Diethers by a Tandem Acid-/Base-Catalyzed Process. Organic Process Research & Development 2020, 24 (2), 154-162.

Leal-Duaso, A.; Pérez, P.; Mayoral, J. A.; García, J. I.; Pires, E., Glycerol-Derived Solvents: Synthesis and Properties of Symmetric Glyceryl Diethers. ACS Sustainable Chemistry & Engineering 2019, 7 (15), 13004-13014.

Lee, C.; Yang, W.; Parr, R. G., Development of the Colle-Salvetti Correlation-Energy Formula into A Functional of the Electron Density. Phys. Rev. B 1988, 37, 785.

Lefebvre, C.; Rubez, G.; Khartabil, H.; Boisson, J.-C.; Contreras-García, J.; Hénon, E., Accurately Extracting the Signature of Intermolecular Interactions Present in the NCI Plot of the Reduced Density Gradient versus Electron Density. Phys. Chem. Chem. Phys. 2017, 19, 17928-17936.

Li, G.; Shang, Y.; Wang, Y.; Wang, L.; Chao, Y.; Qi, Y., Reaction Mechanism of Etherification of Rice Straw with Epichlorohydrin in Alkaline Medium. Scientific Reports 2019, 9 (1), 14307.

Li, J.; Mundhwa, M.; Henni, A., Volumetric Properties, Viscosities, Refractive Indices, and Surface Tensions for Aqueous Genosorb 1753 Solutions. Journal of Chemical & Engineering Data 2007, 52 (3), 955-958.

Liu, X.; O'Harra, K. E.; Bara, J. E.; Turner, C. H., Molecular Insight into the Anion Effect and Free Volume Effect of CO2 Solubility in Multivalent Ionic Liquids. Phys. Chem. Chem. Phys. 2020, 22, 20618-20633.

Liu, X.; O'Harra, K. E.; Bara, J. E.; Turner, C. H., Solubility Behavior of CO2 in Ionic Liquids Based on Ionic Polarity Index Analyses. The Journal of Physical Chemistry B 2021, 125 (14), 3665-3676.

Liu, Z.; Lu, T.; Chen, Q., Intermolecular interaction characteristics of the all-carboatomic ring, cyclo[18]carbon: Focusing on molecular adsorption and stacking. Carbon 2021, 171, 514-523.

Lu, T., Molclus Program, Version 1.9.5. Beijing Kein Research Center for Natural Science, China. <http://www.keinsci.com/research/molclus.html> (accessed Jul. 1, 2020): 2016.

Lu, T.; Chen, F., Multiwfn: A Multifunctional Wavefunction Analyzer. J. Comput. Chem. 2012, 33, 580-592.

Lu, T.; Chen, F., Quantitative Analysis of Molecular Surface Based on Improved Marching Tetrahedra Algorithm. J. Mol. Graph. Model. 2012, 38, 314-323.

Lu, T.; Manzetti, S., Wavefunction and Reactivity Study of Benzo[a]pyrene Diol Epoxide and Its Enantiomeric Forms. Struct. Chem. 2014, 25, 1521-1533.

Murray, J. S.; Brinck, T.; Lane, P.; Paulsen, K.; Politzer, P., Statistically-Based Interaction Indices Derived from Molecular Surface Electrostatic Potentials: A General Interaction Properties Function (GIPF). J. Mol. Struct. Theochem 1994, 307, 55-64.

Neese, F., Software Update: the ORCA Program System, Version 4.0. Wiley Interdiscip. Rev.: Comput. Mol. Sci. 2018, 8, e1327.

Neese, F., The ORCA Program System. Wiley Interdiscip. Rev.: Comput. Mol. Sci. 2012, 2, 73-78.

Nemes, A.; Tölgyesi, L.; Bodor, A.; Rábai, J.; Szabó, D., Greener fluorous chemistry: Convenient preparation of new types of 'CF3-

(56) References Cited

OTHER PUBLICATIONS rich' secondary alkyl mesylates and their use for the synthesis of azides, amines, imidazoles and imidazolium salts. Journal of Fluorine Chemistry 2010, 131 (12), 1368-1376.

Pakzad, P.; Mofarahi, M.; Ansarpour, M.; Afkhamipour, M.; Lee, C.-H., Chapter 3—CO2 absorption by common solvents. In Advances in Carbon Capture, Rahimpour, M. R.; Farsi, M.; Makarem, M. A., Eds. Woodhead Publishing: 2020; pp. 51-87.

Perdew, J. P., Density-Functional Approximation for the Correlation Energy of the Inhomogeneous Electron Gas. Phys. Rev. B 1986, 33, 8822.

Pracht, P.; Bohle, F.; Grimme, S., Automated Exploration of the Low-Energy Chemical Space with Fast Quantum Chemical Methods. Phys. Chem. Chem. Phys. 2020, 22, 7169-7192.

Pracht, P.; Caldeweyher, E.; Ehlert, S.; Grimme, S., A Robust Non-Self-Consistent Tight-Binding Quantum Chemistry Method for large Molecules. ChemRxiv 2019, preprint (DOI: 10.26434/chemrxiv.8326202.v1).

Qian, S.; Liu, X.; Dennis, G. P.; Turner, C. H.; Bara, J. E., Properties of symmetric 1,3-diethers based on glycerol skeletons for CO2 absorption. Fluid Phase Equilibria 2020, 521, 112718.

Qian, S.; Liu, X.; Emel'yanenko, V. N.; Sikorski, P.; Kammakakam, I.; Flowers, B. S.; Jones, T. A.; Turner, C. H.; Verevkin, S. P.; Bara, J. E., Synthesis and Properties of 1,2,3-Triethoxypropane: A Glycerol-Derived Green Solvent Candidate. Industrial & Engineering Chemistry Research 2020, 59 (45), 20190-20200.

Qian, S.; Liu, X.; Turner, C. H.; Bara, J. E., Synthesis and properties of symmetric glycerol-derived 1,2,3-triethers and 1,3-diether-2-ketones for CO2 absorption. Chemical Engineering Science 2022, 248, 117150.

Quispe, C. A. G.; Coronado, C. J. R.; Carvalho Jr, J. A., Glycerol: Production, consumption, prices, characterization and new trends in combustion. Renewable and Sustainable Energy Reviews 2013, 27, 475-493.

Sandoval, M.; Civera, C.; Berenguer, J.; García-Blanco, F.; Hernaiz, M. J., Optimised N-acetyl-d-lactosamine synthesis using Thermus thermophilus β-galactosidase in bio-solvents. Tetrahedron 2013, 69 (3), 1148-1152.

Scholz, E., Karl Fischer titrations of aldehydes and ketones. Analytical Chemistry 1985, 57 (14), 2965-2971.

Shannon, M. S.; Tedstone, J. M.; Danielsen, S. P.; Hindman, M. S.; Irvin, A. C.; Bara, J. E., Free Volume as the Basis of Gas Solubility and Selectivity in Imidazolium-Based Ionic Liquids. Ind. Eng. Chem. Res. 2012, 51, 5565-5576.

Sheldon, R. A., The E Factor: fifteen years on. Green Chemistry 2007, 9 (12), 1273-1283.

Shiflett, M. B.; Yokozeki, A., Solubilities and Diffusivities of Carbon Dioxide in Ionic Liquids: [bmim][PF6] and [bmim][BF4]. Industrial & Engineering Chemistry Research 2005, 44 (12), 4453-4464.

Shukla, S. K.; Khokarale, S. G.; Bui, T. Q.; Mikkola, J.-P. T., Ionic Liquids: Potential Materials for Carbon Dioxide Capture and Utilization. Frontiers in Materials 2019, 6 (42).

Singh, G. S.; Mollet, K.; D'hooghe, M.; De Kimpe, N., Epihalohydrins in Organic Synthesis. Chemical Reviews 2013, 113 (3), 1441-1498.

Sugiyama, H.; Hattori, Y., Selective and enhanced CO2 adsorption on fluorinated activated carbon fibers. Chemical Physics Letters 2020, 758, 137909.

Sun, D.; Yamada, Y.; Sato, S.; Ueda, W., Glycerol as a potential renewable raw material for acrylic acid production. Green Chemistry 2017, 19 (14), 3186-3213.

Sutter, M.; Silva, E. D.; Duguet, N.; Raoul, Y.; Métay, E.; Lemaire, M., Glycerol Ether Synthesis: A Bench Test for Green Chemistry Concepts and Technologies. Chemical Reviews 2015, 115 (16), 8609-8651.

Tan, H. W.; Abdul Aziz, A. R.; Aroua, M. K., Glycerol production and its applications as a raw material: A review. Renewable and Sustainable Energy Reviews 2013, 27, 118-127.

Trost, B., The atom economy—a search for synthetic efficiency. Science 1991, 254 (5037), 1471-1477.

Urata, K.; Yano, S.; Kawamata, A .; Takaishi, N.; Inamoto, Y., A convenient synthesis of long-chain 1-O-Alkyl glyceryl ethers. Journal of the American Oil Chemists' Society 1988, 65 (8), 1299-1302.

Wang, C.; Luo, X.; Luo, H.; Jiang, D.-e.; Li, H.; Dai, S., Tuning the Basicity of Ionic Liquids for Equimolar CO2 Capture. Angewandte Chemie International Edition 2011, 50 (21), 4918-4922.

Wang, R.; Song, L.; Guo, Y.; Kou, J.; Song, H.; Liu, Y.; Zhang, J.; Wang, Q., Synthesis and structure-activity relationships of nonionic surfactants with short fluorocarbon chains. Journal of Molecular Liquids 2021, 321, 114486.

Zaffalon, P.-L.; Zumbuehl, A., BODP—A Versatile Reagent for Phospholipid Synthesis. Synthesis 2011, 2011, 778-782.

Zhao, Y.; Truhlar, D. G., The M06 Suite of Density Functionals for Main Group Thermochemistry, Thermochemical Kinetics, Noncovalent Interactions, Excited States, and Transition Elements: Two New Functionals and Systematic Testing of Four M06-Class Functionals and 12 Other Functionals. Theor. Chem. Acc. 2008, 120, 215-241.

* cited by examiner

COMPOUNDS FOR SOLUBILIZING POLYMERS

CROSS-REFERENCE TO RELATED APPLICATION

This application claims the benefit of U.S. Provisional Application 63/196,894, filed on Jun. 4, 2021, the contents of which are hereby incorporated in its entirety.

ACKNOWLEDGEMENT OF GOVERNMENT SUPPORT

This invention was made with government support under Grant No. 2029387 awarded by National Science Foundation. The government has certain rights in the invention.

FIELD OF THE INVENTION

The invention is directed to compounds for solubilizing polymers, and methods of solubilizing polymers using compounds disclosed herein.

BACKGROUND

Since the advent of the mass production of plastics for consumer goods in the early/mid-20$^{th}$ Century, just ~9% of all plastic ever produced has been recycled. While collection and recycling rates have increased over time, ~79% of all plastics ever made have ended up in landfills and/or have been released into natural environments. Furthermore, recycling processes (e.g., melting) are detrimental to the physical and mechanical properties and the resultant materials are generally inferior to virgin plastics due to reductions in molecular weight (MW). This is in stark contrast to other common recyclables such as aluminum, where ~50% of beverage cans are recycled annually and ~75% of all aluminum produced since 1888 is still in use today, with virtually no difference in properties between recycled and new aluminum.

Once in the environment, plastic wastes are prone to form smaller particles known as microplastics, release toxic plasticizers and additives, and affect plant and animal life at all levels. The "Great Pacific Garbage Patch" is a notorious example of the excesses of our mismanagement and lack of attention of plastic waste. Polyethylene (PE), polypropylene (PP), poly(vinyl chloride) (PVC), and polyethylene terephthalate (PET) make up the large majority of this waste, and are thus the primary plastics polluting the environment. There remains a need for methods to "upcycle" (rather than recycle) these wastes into value-added products.

The conversion of plastic materials into their constituent monomer starting materials is a highly desirable process, and would enable the broadest levels of plastic re-use. However, efficient methods for "de-polymerizing" plastic materials remain elusive, partly due to the low solubility of polymeric and oligomeric compounds in solvents. There remains a need for improved solvents capable of dissolving polymeric and oligomeric compounds, thereby facilitating de-polymerization reactions to convert these materials into monomers.

The removal of carbon dioxide, dihydrogen sulfide, and other undesirable compounds from hydrocarbon gas streams is an important industrial process. In the Selexol® process, currently in use throughout the world, a hydrocarbon feedstock is passed through a solvent (typically dimethyl ethers of polyethylene glycol (DMPEG)) at high pressure. The solvent dissolves undesirable chemicals, enabling their removal from the hydrocarbon. While DMPEG has many desirable attributes, a solvent with higher capacity for COs, $H_2S$, and other compounds would still represent a significant advance. Ionic liquids have been explored as substitutes for DMPEG, but have not been widely adopted due to limitations stemming from their high viscosities. There remains a need for improved solvents for the removal of $CO_2$, $H_2S$ and other compounds from hydrocarbon gas streams.

SUMMARY

Disclosed herein are glycerol derived ketone and acetal-based solvents. The solvents are easily prepared in large scale from readily available starting materials and reagents. The solvents disclosed herein are useful for dissolving and solubilizing polymeric and oligomeric compounds. The solvents are useful for dissolving and separating contaminant compounds from hydrocarbon gas streams.

In accordance with the purposes of the disclosed materials and methods, as embodied and broadly described herein, the disclosed subject matter, in one aspect, relates to compounds, compositions and methods of making and using compounds and compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments are set forth in the descriptions below. Other features, objects, and advantages will be apparent from the description and from the claims.

DETAILED DESCRIPTION

Figure 1:
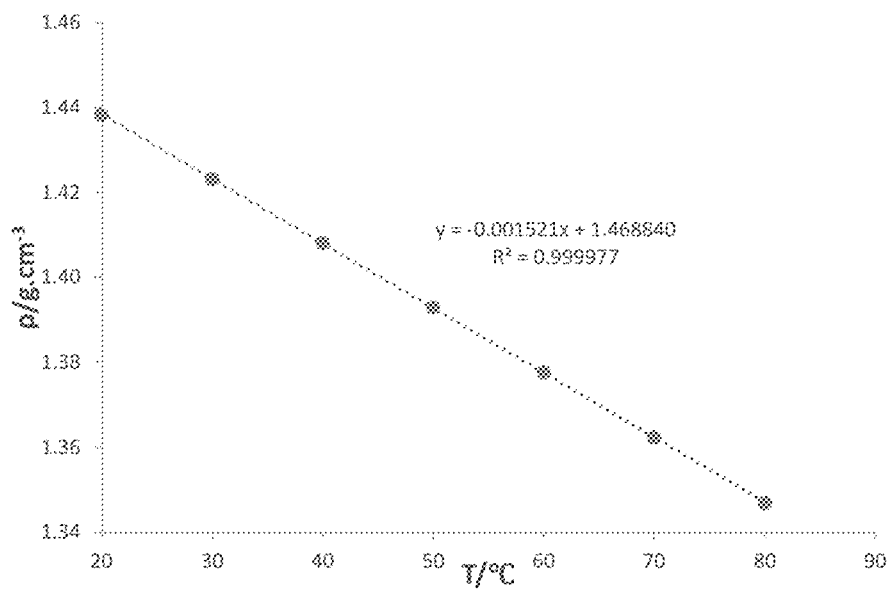
FIG. 1 depicts the density of DTEPK in temperature range of 20 to 80° C.
Figure 2:
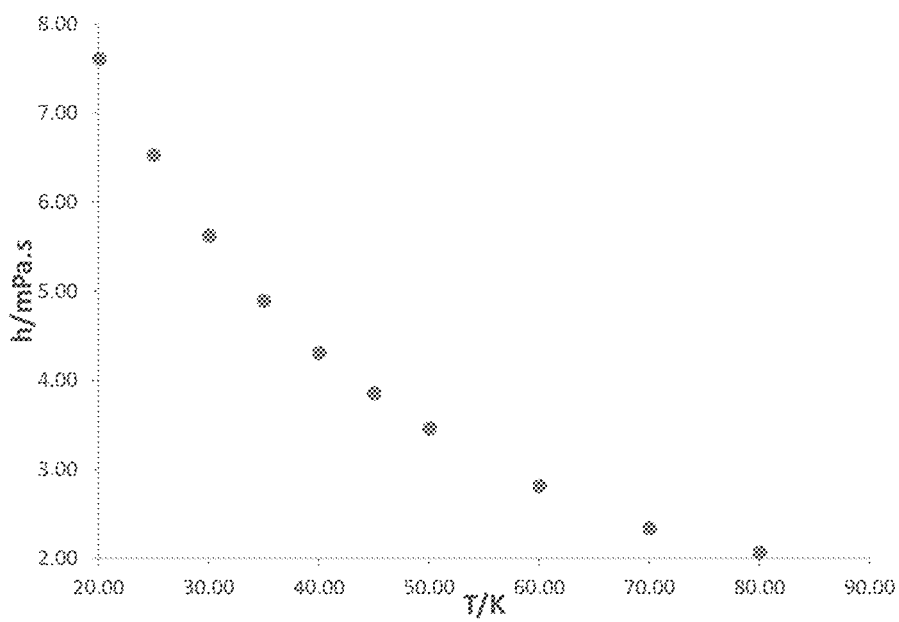
FIG. 2 depicts the viscosity of DTEPK in temperature range of 20 to 80° C.
Figure 3:
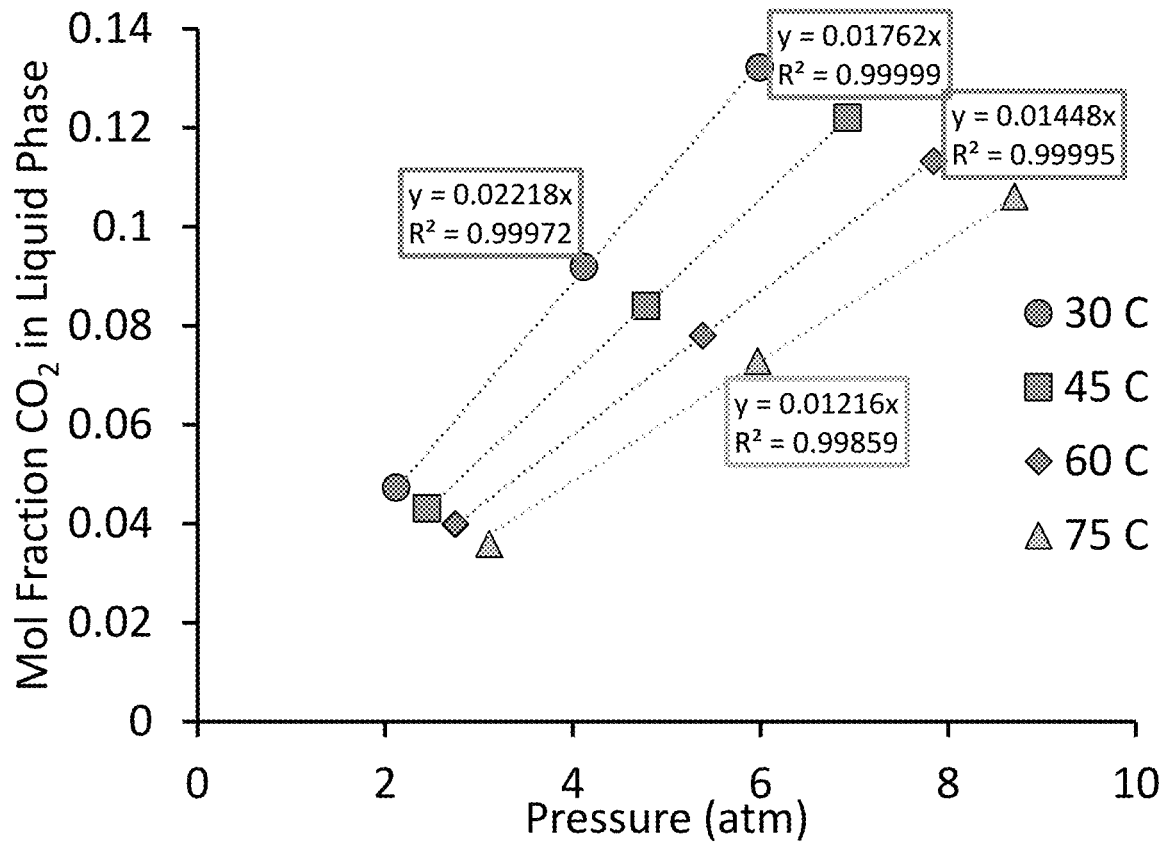
FIG. 3 depicts the $CO_2$ absorption performance of DTEPK.
Figure 4:
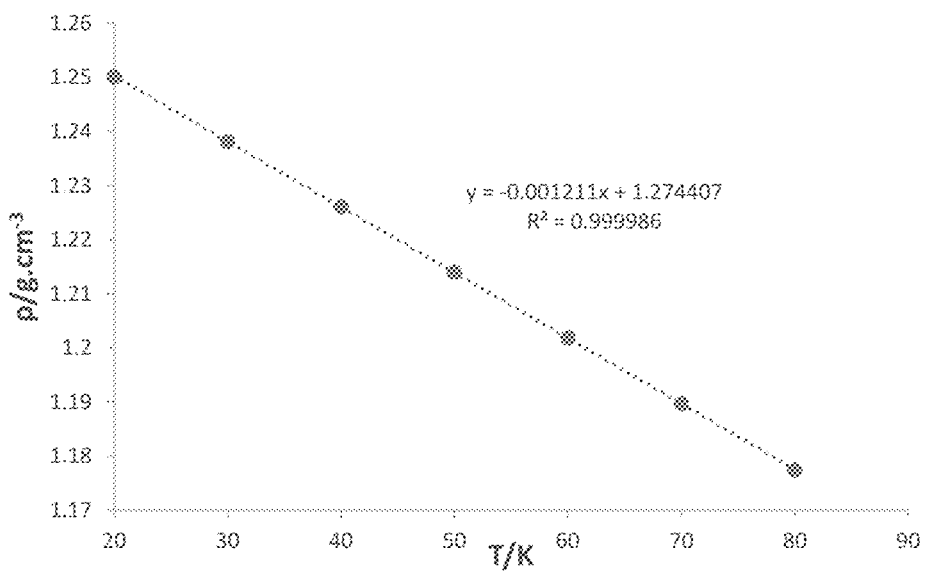
FIG. 4 depicts the density of AMTEPK in temperature range of 20 to 80° C.
Figure 5:
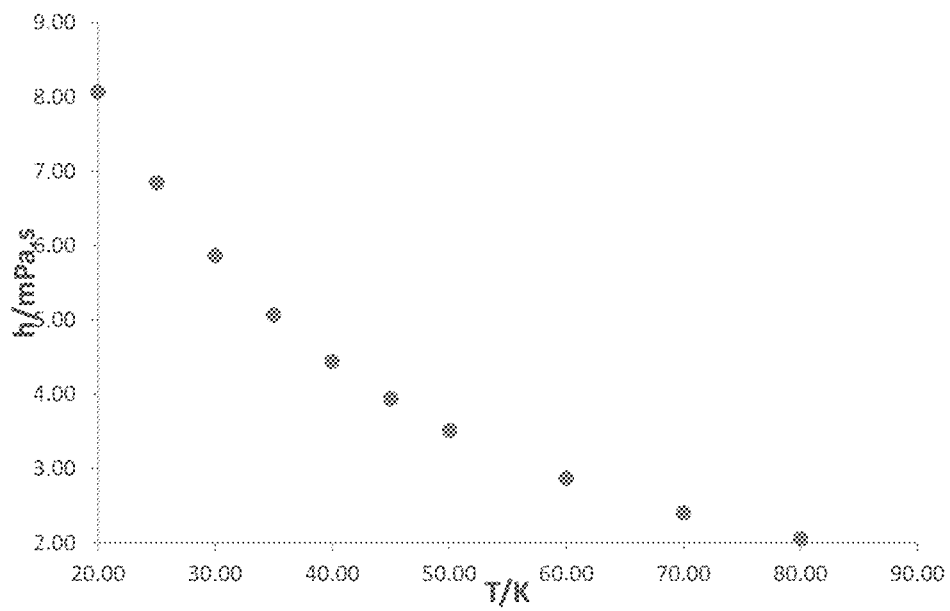
FIG. 5 depicts the viscosity of AMTEPK in temperature range of 20 to 80° C.
Figure 6:
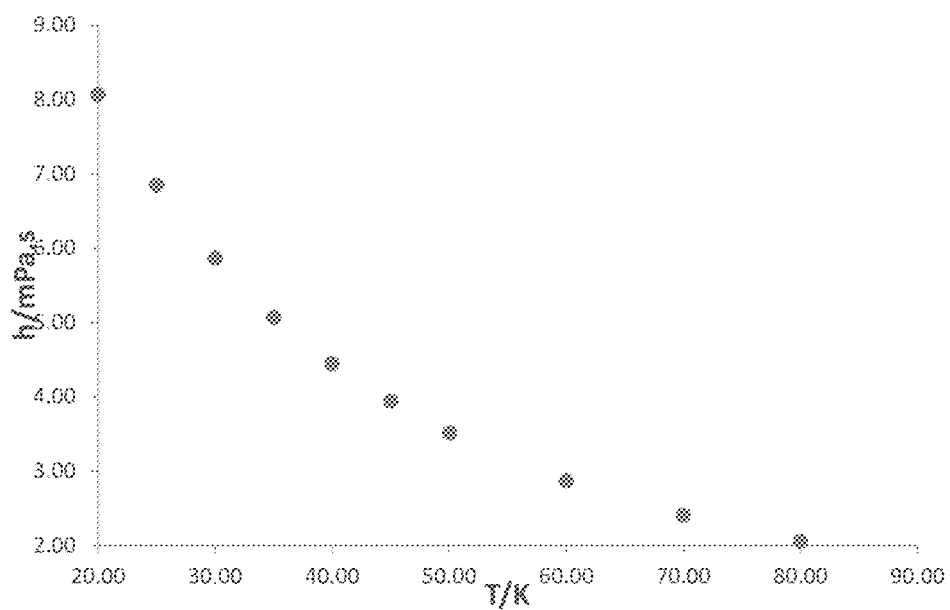
FIG. 6 depicts the $CO_2$ absorption performance of AMTEPK.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value.

When such a range is expressed, another embodiment includes-, from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cyloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. A cycloalkyl group which contains no double or triple carbon-carbon bonds is designated a saturated cycloalkyl group, whereas a cycloalkyl group having one or more such bonds (yet is still not aromatic) is designated an unsaturated cycloalkyl group. Unless specified to the contrary, the term cycloalkyl embraces both saturated and unsaturated, non-aromatic, ring systems.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyL cirrnolinyl, decahydroquinolinyl, 2H,6H~1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy," "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent can be substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. In a specific example, groups that are said to be substituted are substituted with a protic group, which is a group that can be protonated or deprotonated, depending on the pH.

As used herein, the abbreviation [E,K,E] refers to the compound 1,3-diethoxypropan-2-one.

As used herein, the abbreviation [ME, K, ME] refers to the compound 2,5,9,12-tetraoxatridecan-7-one (CAS 130670-58-5).

As used herein, the abbreviation [F,K,F] refers to the compound 1,3-bis(2,2,2-trifluoroethoxy)propan-2-one.

As used herein, the abbreviation [ME,ME,ME] refers to the compound 7-(2-methoxyethoxy)-2,5,9,12-tetraoxatridecane, having the formula:

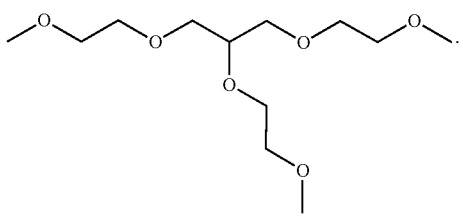

As used herein, the abbreviation [F,ME,F] refers to the compound 2-(2-methoxyethoxy)-1,3-bis(2,2,2-trifluoroethoxy)propane, having the formula:

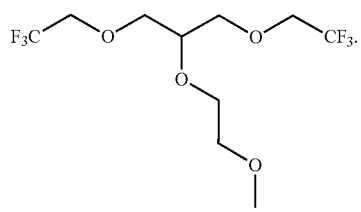 [SMILES: COCCOC(COCC(F)(F)F)COCC(F)(F)F]

Disclosed herein are compounds and methods for solubilizing a polymer, in which the polymer is contacted with one or more compounds of Formula (I):

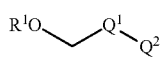

[Formula (I)]

wherein $R^1$ is selected from: $C_{1-10}$alkyl; $C_{6-18}$aryl; $C_{3-10}$cycloalkyl; $C_{1-10}$heteroalkyl; $C_{6-18}$ heterocyclyl;

$Q^1$ represents a moiety having the structure:

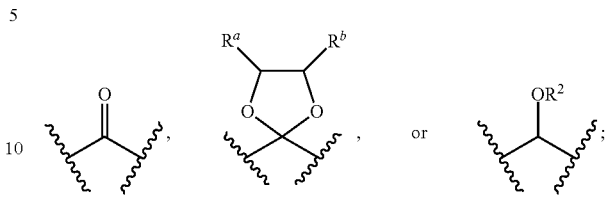

$Q^2$ represents a moiety having the structure:

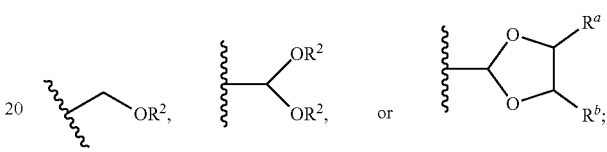

wherein $R^2$ is selected from: hydrogen; $C_{1-10}$alkyl; $C_{6-18}$aryl; $C_{3-10}$cycloalkyl; $C_{1-10}$heteroalkyl; $C_{6-18}$heterocyclyl, one of $R^a$ and $R^b$ is hydrogen, and the other is —$CH_2OR^3$ wherein $R^3$ is selected from: hydrogen; $C_{1-10}$alkyl; $C_{6-18}$aryl; $C_{3-10}$cycloalkyl; $C_{1-10}$heteroalkyl; $C_{6-18}$ heterocyclyl, wherein $Q^1$ and $Q^2$ do not both include an $R^2$ group; and also wherein $Q^1$ and $Q^2$ do not both include an $R^3$ group.

In some embodiments, $R^1$ is a $C_{1-10}$alkyl group, a $C_{1-6}$alkyl group, or a $C_{1-4}$alkyl group, in each case optionally substituted one or more times by Cl, F, Br, I, $C_{6-18}$aryl, $C_{1-10}$alkoxy, or $C_{1-10}$ haloalkoxy. Exemplary $R^1$ groups include methyl, ethyl, n-propyl, isopropyl, n-butyl, isobutyl, tert-butyl, sec-butyl, trifluoromethyl, 2,2,2-trifluoroethyl, 2,2,3,3,3-pentafluoropropyl, hexafluoroisopropyl, 2-methoxyethyl, 2-trifluoromethoxyethyl, benzyl, 4-fluorobenzyl, 4-trifluoromethylbenzyl, 4-methoxybenzyl, 2-fluorobenzyl, 2-trifluoromethylbenzyl, 2-methoxybenzyl, 3-fluorobenzyl, 3-trifluoromethylbenzyl, and 3-methoxybenzyl. In exemplary embodiments, $R^1$ is $C_{1-4}$alkyl group, substituted one or more times by F or $C_{1-10}$alkoxy.

In some embodiments, $R^2$ is a $C_{1-10}$alkyl group, a $C_{1-6}$alkyl group, or a $C_{1-4}$alkyl group, in each case optionally substituted one or more times by Cl, F, Br, I, $C_{6-18}$aryl, $C_{1-10}$alkoxy, or $C_{1-10}$haloalkoxy. Exemplary $R^2$ groups include methyl, ethyl, n-propyl, isopropyl, n-butyl, isobutyl, tert-butyl, sec-butyl, trifluoromethyl, 2,2,2-trifluoroethyl, 2,2,3,3,3-pentafluoropropyl, hexafluoroisopropyl, 2-methoxyethyl, 2-trifluoromethoxyethyl, benzyl, 4-fluorobenzyl, 4-trifluoromethylbenzyl, 4-methoxybenzyl, 2-fluorobenzyl, 2-trifluoromethylbenzyl, 2-methoxybenzyl, 3-fluorobenzyl, 3-trifluoromethylbenzyl, and 3-methoxybenzyl. In exemplary embodiments, $R^2$ is $C_{1-4}$alkyl group, substituted one or more times by F or $C_{1-10}$alkoxy.

In certain embodiments, the compound has the formula:

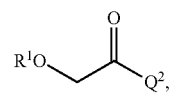

In some embodiments, the compound can be a compound of Formula (II), Formula (III), or Formula (IV):

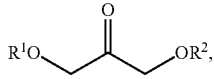
[Formula (II)]

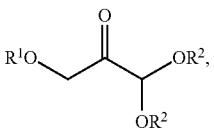
[Formula (III)]

or

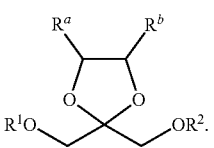
[Formula (IV)]

In the compound of Formula (IV), when $R^1$ is different than $R^2$, two possible regioisomeric acetal compounds are possible, e.g. Formula (IVa) and Formula (IVb),

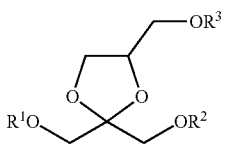
[Formula (IVa)]

and

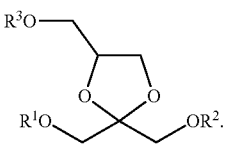
[Formula (IVb)]

The skilled person understands that the nature of $R^1$, $R^2$, and $R^3$, as well as the process used to prepare the compound can all influence whether one regioisomer (i.e., Formula (IVa) vs.

Formula (IVb)) predominates over the other. Unless specified to the contrary, as used herein reference to the compound:

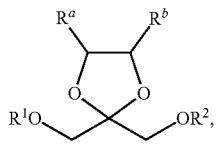

refers to each of the individual isomers, as well as mixtures of the two isomers in any ratio.

In certain embodiments, the compound is a compound of Formula (V):

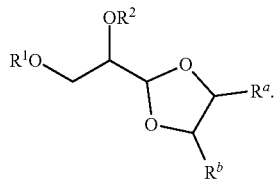
[Formula (V)]

The discussion above regarding regioisomeric acetal compounds at the $Q^1$ position is also applicable to regioisomeric acetal compounds at the $Q^2$ position:

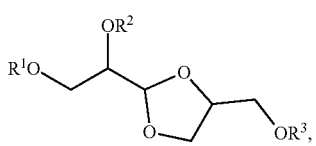
[Formula (Va)]

and

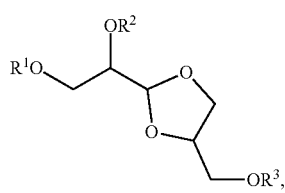
[Formula (Vb)]

either as single regioisomers as well as mixtures of Formula (Va) and Formula (Vb).

The skilled person appreciates that the acetal compounds of Formula (IV), (IVa), (IVb), (V), (Va), and (Vb) may exist as one of several stereoisomeric compounds. Unless stated otherwise to the contrary, the depiction of a compound without conventional hashes and wedges embraces all possible stereoisomers, either as a single isomer or a mixture of two or more isomers.

In some embodiments, the compound of Formula (1) is defined when $R^1$ is $C_{1-10}$alkyl, optionally substituted one or more times by $R^{1a}$, $OR^{1a}$, $N(R^{1a})_2$, $SiR^{1a}{}_3$, $SR^{1ar}$, $SO_2R^{1a}$, $SO_2N(R^{1a})_2$, $C(O)R^{1a}$; $C(O)OR^{1a}$, $OCOR^{1a}$; $C(O)N(R^{1a})_2$, $OC(O)N(R^{1a})_2$, $N(R^{1a})C(O)N(R^{1a})_2$, F, Cl, Br, I, cyano, and nitro, wherein $R^{1a}$ is in each case independently selected from hydrogen, $C_{1-10}$ alkyl; $C_{6-18}$ aryl; $C_{3-10}$cycloalkyl; $C_{1-10}$heteroalkyl; $C_{6-18}$heterocyclyl; wherein any two or more of $R^{1a}$ may together form a ring.

The compound of Formula (1) or Formula (1a) may also be defined where $R^1$ has the formula:

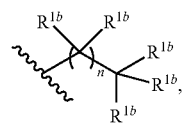

wherein n is selected from 0-9, and $R^{1b}$ is in each case independently selected from F, Cl, Br, I, cyano, nitro, $R^{1b}$, and $OR^{1b}$, wherein $R^{1b}$ is in each case independently selected from hydrogen, $C_{1-10}$alkyl; $C_{6-18}$aryl; $C_{3-10}$cycloalkyl; $C_{1-10}$heteroalkyl; $C_{6-18}$ heterocyclyl; wherein any two or more of $R^{1b}$ may together form a ring.

Suitable values for n include 0, 1, 2, 3, 4, 5, 6, 7, 8, or 9.

In some instances, $R^{1b}$ is in each case independently selected from hydrogen and F. Particularly preferred values of n include 0, 1, and 2. In some embodiments, each $R^{1b}$ is F.

In certain embodiments, $R^1$ has the formula:

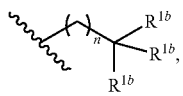

wherein n is 0-9, and $R^{1b}$ is independently selected from hydrogen and F. Particularly preferred values of n include 0, 1, and 2. In some embodiments, each $R^{1b}$ is F.

The compound of Formula (1) or Formula (1a) may also be defined where $R^1$ has the formula:

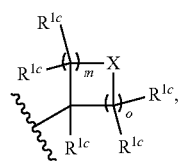

wherein m is from 0-9, o is from 0-9, wherein the sum of m+o does not exceed 9;

X is selected from O, S, $NR^{1c'}$;

$R^{1c}$ is in each case independently selected from F, Cl, Br, I, $R^{1c'}$, $OR^{ic'}$, wherein $R^{1c'}$ is in each case independently selected from hydrogen, $C_{1-10}$ alkyl; $C_{6-18}$aryl; $C_{3-10}$cycloalkyl; $C_{1-10}$ heteroalkyl; $C_{6-18}$heterocyclyl; wherein any two or more of $R^{1c}$ may together form a ring.

The compound of Formula (1) or Formula (1a) may also be defined where X is O. Exemplary values for m and o include embodiments wherein m and o are both 2, and also in embodiments in which m is 1 and o is 2. In some cases, $R^{1c}$ is selected from hydrogen and F, and in others $R^{1c}$ is in each case hydrogen.

The compound of Formula (1) or Formula (1a) may also be defined where $R^1$ has the formula:

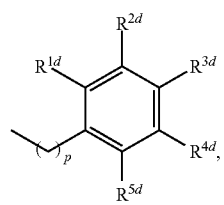

wherein p is selected from 0-9;

$R^{1d}$ is selected from hydrogen, F, Cl, Br, I, cyano, nitro, $R^{1d'}$, and $OR^{1d'}$, wherein $R^{1d'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$ heterocyclyl;

$R^{2d}$ is selected from hydrogen, F, Cl, Br, I, cyano, nitro, $R^{2d'}$, and $OR^{2d'}$, wherein $R^{2d'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl;

$R^{3d}$ is selected from hydrogen, F, Cl, Br, I, cyano, nitro, $R^{3d'}$, and $OR^{3d'}$, wherein $R^{3d'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl;

$R^{4d}$ is selected from hydrogen, F, Cl, Br, I, cyano, nitro, $R^{4d'}$, and $OR^{4d'}$, wherein $R^{4d'}$ is in each case independently selected from hydrogen, $C_{1-10}$alkyl; $C_{6-18}$aryl; $C_{3-10}$cycloalkyl; $C_{1-10}$heteroalkyl; $C_{6-18}$heterocyclyl;

$R^{5d}$ is selected from hydrogen, F, Cl, Br, I, cyano, nitro, $R^{5d'}$, and $OR^{5d'}$, wherein $R^{5d'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl;

wherein any two or more of $R^{1d'}$, $R^{2d'}$, $R^{3d'}$, $R^{4d'}$, and $R^{5d'}$ may together form a ring.

Suitable values for p include 0 or 1.

In exemplary embodiments, $R^{1d}$ is selected from hydrogen, F, or $OR^{1d'}$, wherein $R^{1d'}$ is in each case independently selected from $C_{1-10}$alkyl.

In exemplary embodiments, $R^{2d}$ is selected from hydrogen, F, or $OR^{2d'}$, wherein $R^{2d'}$ is in each case independently selected from $C_{1-10}$alkyl.

In exemplary embodiments, $R^{3d}$ is selected from hydrogen, F, or $OR^{3d'}$, wherein $R^{3d'}$ is in each case independently selected from $C_{1-10}$alkyl.

In exemplary embodiments, $R^{4d}$ is selected from hydrogen, F, or $OR^{4d'}$, wherein $R^{4d'}$ is in each case independently selected from $C_{1-10}$alkyl.

In exemplary embodiments, $R^{5d}$ is selected from hydrogen, F, or $OR^{5d'}$, wherein $R^{5d'}$ is in each case independently selected from $C_{1-10}$alkyl.

Disclosed herein are compound of Formula (1) where $R^2$ is $C_{1-10}$alkyl, optionally substituted one or more times by $R^{2e}$, $OR^{2e}$, $N(R^{2e})_2$, $SiR^{2er}$, $SR^{2er}$, $SO_2R^{2e}$, $SO_2N(R^{2e})_2$, $C(O)R^{2e}$; $C(O)OR^{2e}$, $OCOR^{2e}$; $C(O)N(R^{2e})_2$, $OC(O)N(R^{2e})_2$, $N(R^{2e})C(O)N(R^{2e})_2$, F, Cl, Br, I, cyano, and nitro, wherein $R^{2e}$ is in each case independently selected from hydrogen, $C_{1-10}$alkyl; $C_{6-18}$aryl; $C_{3-10}$cycloalkyl; $C_{1-10}$heteroalkyl; $C_{6-18}$heterocyclyl; wherein any two or more of $R^{2e}$ may together form a ring.

In some embodiments of the compound of Formula (1), $R^2$ can be hydrogen, or can has the formula:

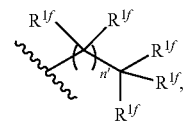

wherein n' is selected from 0-9, and $R^{1f}$ is in each case independently selected from F, Cl, Br, I, cyano, nitro, $R^{1f'}$, and $OR^{1f'}$, wherein $R^{1f'}$ is in each case independently selected from hydrogen, $C_{1-10}$alkyl; $C_{6-18}$aryl; $C_{3-10}$cycloalkyl; $C_{1-10}$heteroalkyl; $C_{6-18}$heterocyclyl; wherein any two or more of $R^{1f'}$ may together form a ring.

Exemplary values of n' include 0, 1, 2, 3, 4, 5, 6, 7, 8, and 9. $R^{1f}$ can in each case independently selected from hydrogen and F.

In some embodiments of the compound of Formula (1), $R^2$ has the formula:

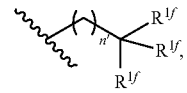

wherein n' is 0-9, and $R^{1f}$ is independently selected from hydrogen and F.

In some cases, n' is 0, 1, or 2, and $R^{1f}$ is in each case F.

In some embodiments of the compound of Formula (1), $R^2$ has the formula:

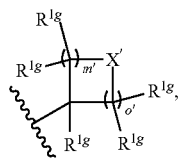

wherein m' is from 0-9, o' is from 0-9, wherein the sum of m'+o' does not exceed 9;

X' is selected from O, S, $NR^{1g'}$;

$R^{1g}$ is in each case independently selected from F, Cl, Br, I, $R^{1g'}$, $OR^{1g'}$, wherein $R^{1g'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl; wherein any two or more of $R^{1c}$ may together form a ring.

In some embodiments X' is O.

Exemplary values for m' and o' include those wherein m' and o' are both 2, and also where m' is 1 and o' is 2.

In certain embodiments $R^{1g}$ is selected from hydrogen and F, for instance, $R^{1g}$ is in each case hydrogen.

In some embodiments of the compound of Formula (1), $R^2$ has the formula:

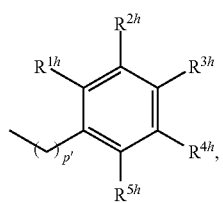

wherein p' is selected from 0-9;

$R^{1h}$ is selected from hydrogen, F, Cl, Br, I, cyano, nitro, $R^{1h'}$, and $OR^{1h'}$, wherein $R^{1h'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$heterocyclyl;

$R^{2h}$ is selected from hydrogen, F, Cl, Br, I, cyano, nitro, $R^{2h'}$, and $OR^{2h'}$, wherein $R^{2h'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl;

$R^{3h}$ is selected from hydrogen, F, Cl, Br, I, cyano, nitro, $R^{3h'}$, and $OR^{3h'}$, wherein $R^{3h'}$ is in each case independently selected from hydrogen, $C_{1-10}$alkyl; $C_{6-18}$aryl; $C_{3-10}$cycloalkyl; $C_{1-10}$ heteroalkyl; $C_{6-18}$heterocyclyl;

$R^{4h}$ is selected from hydrogen, F, Cl, Br, I, cyano, nitro, $R^{4h'}$, and $OR^{4h'}$, wherein $R^{4h'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl;

$R^{5h}$ is selected from hydrogen, F, Cl, Br, I, cyano, nitro, $R^{5h'}$, and $OR^{5h'}$, wherein $R^{5h'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl; wherein any two or more of $R^{1h'}$, $R^{2h'}$, $R^{3h'}$, $R^{4h'}$, and $R^{5h'}$ may together form a ring.

Exemplary compounds include those wherein p' is 0 or 1.

Exemplary compounds include those wherein $R^{1h}$ is selected from hydrogen, F, or $OR^{1h'}$, wherein $R^{1h'}$ is in each case independently selected from $C_{1-10}$alkyl.

Exemplary compounds include those wherein $R^{2h}$ is selected from hydrogen, F, or $OR^{2h'}$, wherein $R^{2h'}$ is in each case independently selected from $C_{1-10}$alkyl.

Exemplary compounds include those wherein $R^{3h}$ is selected from hydrogen, F, or $OR^{3h'}$ wherein $R^{3h'}$ is in each case independently selected from $C_{1-10}$alkyl.

Exemplary compounds include those wherein $R^{4h}$ is selected from hydrogen, F, or $OR^{4h'}$ wherein $R^{4h'}$ is in each case independently selected from $C_{1-10}$alkyl.

Exemplary compounds include those wherein $R^{5d}$ is selected from hydrogen, F, or $OR^{5h'}$ wherein $R^{5h'}$ is in each case independently selected from $C_{1-10}$alkyl.

In some embodiments of the compound of Formula (I), $R^3$ has the formula:

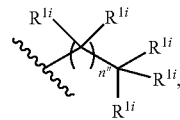

wherein n" is selected from 0-9, and $R^{1i}$ is in each case independently selected from F, Cl, Br, I, cyano, nitro, $R^{1i'}$, and $OR^{1i'}$, wherein $R^{1i'}$ is in each case independently selected from hydrogen, $C_{1-10}$alkyl; $C_{6-18}$ aryl; $C_{3-10}$ cycloalkyl; $C_{1-10}$heteroalkyl; $C_{6-18}$ heterocyclyl; wherein any two or more of $R^{1i'}$ may together form a ring.

Suitable values for n" include 1, 2, 3, 4, 5, 6, 7, 8, and 9.

In certain embodiments, $R^{1i}$ is in each case independently selected from hydrogen and F, for example, $R^3$ can have the formula:

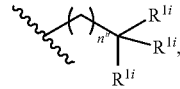

wherein n" is 0-9, and $R^{1i}$ is independently selected from hydrogen and F.

For such compounds, n" can be 0, 1, or 2, and R" is in each case F.

In other embodiments, $R^3$ has the formula:

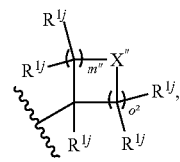

wherein m" is from 0-9, o" is from 0-9, wherein the sum of m"+o" does not exceed 9; X" is selected from O, S, $NR^{1j'}$;

$R^{1j}$ is in each case independently selected from F, Cl, Br, I, $R^{1j'}$, $OR^{1j'}$, wherein $R^{1j'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl; wherein any two or more of $R^{1j}$ may together form a ring.

In certain embodiments X" is O.

Exemplary values of m" and o" include when both are 2, as well as when m" is 1 and o" is 2.

In certain embodiments, $R^{1j}$ is selected from hydrogen and F, for example $R^{1j}$ can be in each case hydrogen.

In further embodiments, $R^3$ has the formula:

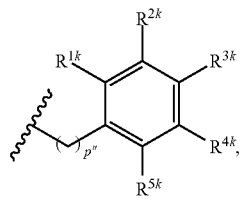

wherein p" is selected from 0-9;
$R^{1k}$ is selected from hydrogen, F, Cl, Br, I, cyano, nitro, $R^{1k'}$, and $OR^{1k'}$, wherein $R^{1k'}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl;
$R^{2k}$ is selected from hydrogen, F, Cl, Br, I, cyano, nitro, $R^{2k'}$, and $OR^{2k'}$, wherein $R^{2k'}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl;
$R^{3k}$ is selected from hydrogen, F, Cl, Br, I, cyano, nitro, $R^{3k'}$, and $OR^{3k'}$, wherein $R^{3k'}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl;
$R^{4k}$ is selected from hydrogen, F, Cl, Br, I, cyano, nitro, $R^{4k'}$, and $OR^{4k'}$, wherein $R^{4k'}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl;
$R^{5k}$ is selected from hydrogen, F, Cl, Br, I, cyano, nitro, $R^{5k'}$, and $OR^{5k'}$, wherein $R^{5k'}$ is in each case independently selected from hydrogen, $C_{1-10}$ alkyl; $C_{6-18}$aryl; $C_{3-10}$ cycloalkyl; $C_{1-10}$heteroalkyl; $C_{6-18}$ heterocyclyl;
wherein any two or more of $R^{1k'}$, $R^{2k'}$, $R^{3k'}$, $R^{4k'}$, and $R^{5k'}$ may together form a ring.

Exemplary values for p" include 0 or 1.
In certain embodiments, $R^{1k}$ is selected from hydrogen, F, or $OR^{1k'}$, wherein $R^{1k'}$ is in each case independently selected from $C_{1-10}$ alkyl.
In certain embodiments, $R^{2k}$ is selected from hydrogen, F, or $OR^{2k'}$, wherein $R^{2k'}$ is in each case independently selected from $C_{1-10}$ alkyl.
In certain embodiments, $R^{3k}$ is selected from hydrogen, F, or $OR^{3k'}$, wherein $R^{3k'}$ is in each case independently selected from $C_{1-10}$ alkyl.
In certain embodiments, $R^{4k}$ is selected from hydrogen, F, or $OR^{4k'}$, wherein $R^{4k'}$ is in each case independently selected from $C_{1-10}$ alkyl.
In certain embodiments, $R^{5d}$ is selected from hydrogen, F, or $OR^{5k'}$, wherein $R^{5k'}$ is in each case independently selected from $C_{1-10}$ alkyl.

The compounds disclosed herein may be used to solubilize a variety of polymers, for example polyethylene, polypropylene, polyethylene terephthalate, polyvinylchloride, polystyrene; polyacrylonitrile, polychloroprene, polytetrafluoroethylene, polyamide, for example nylon, Kevlar, or Nomex, and mixtures thereof.

The compounds disclosed herein may be used to solubilize a polymer having a variety of different molecular weights, for example the polymer can have a molecular weight from 2,500-100,000 Da, from 5,000-100,000 Da, from 7,500-100,000 Da, from 10,000-100,000 Da, from 2,500-50,000 Da, from 2,500-25,000 Da, from 5,000-25,000 Da, or from 5,000-15,000 Da.

For example, the polymer can have a molecular weight of at least 100,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, no greater than 600,000 Da, no greater than 500,000 Da, no greater than 400,000 Da, no greater than 300,000 Da, no greater than 200,000 Da.

In some embodiments, the polymer can have a molecular weight of at least 250,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, no greater than 600,000 Da, no greater than 500,000 Da, no greater than 400,000 Da, or no greater than 300,000 Da.

In some embodiments, the polymer can have a molecular weight of at least a molecular weight of at least 500,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, or no greater than 600,000 Da.

In some embodiments, the polymer can have a molecular weight of at least a molecular weight of at least 750,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, or no greater than 800,000 Da.

In some embodiments, the polymer can have a molecular weight of at least a molecular weight of at least 1,000,000 Da, and no greater than 10,000,000 Da, no greater than 7,500,000 Da, no greater than 5,000,000 Da, no greater than 2,500,000 Da, no greater than 2,000,000 Da, or no greater than 1,500,000 Da.

The compounds of Formula (II) may be prepared by reaction of one or more alcohols with epichlorohydrin or analog thereof. For cases in which $R^1$ and $R^2$ are the same, the compounds may be prepared by first reacting epichlorohydrin with an excess amount of alcohol, followed by oxidation:

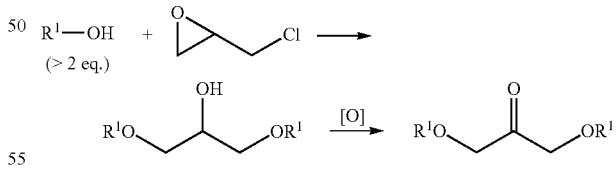

The first reaction may be carried out under activating conditions, e.g., heat, base, Lewis acid, combinations thereof, etc. In certain embodiments, the secondary alcohol intermediate is isolated and/or purified prior to oxidation, while in other embodiments, the nucleophilic opening and oxidation are performed in the same pot, for instance without purification.

For cases in which $R^1$ and $R^2$ are not the same, the compounds may be obtained through sequential reaction of the corresponding alcohols with epichlorohydrin or analog thereof:

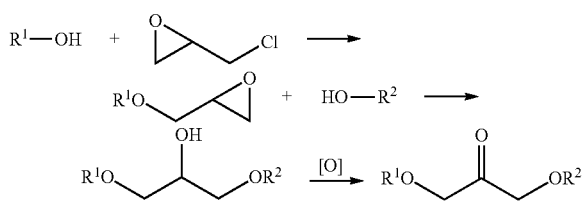

The intermediate epoxide may be isolated prior to reaction with R²—OH, or the second alcohol may be added to the reaction mixture once the first alcohol has been consumed.

In a preferred embodiment, the alcohol(s) and epichlorohydrin analog are combined in an aqueous base medium, for instance sodium hydroxide. The reaction medium may further be heated as necessary to ensure complete reactivity.

Compounds of Formula (IV) may be obtained by condensation of a compound of Formula (II) with a diol having the formula:

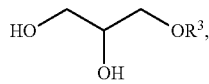

wherein $R^3$ is defined above. The condensation may be conducted using acidic conditions, optionally further in the presence of heat. To drive the equilibrium to the desired product, water may be continuously removed from the reaction mixture.

Compounds of Formula (V) may be obtained by similar condensation of an aldehyde having the formula:

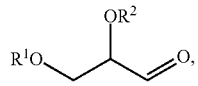

with a diol having the formula:

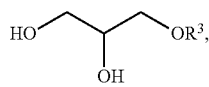

wherein $R^1$, $R^2$, and $R^3$ are as defined above. The aldehyde may be prepared using conventional chemistries, for example oxidative cleave of an appropriate precursor olefin, or orthogonal protecting group manipulations:

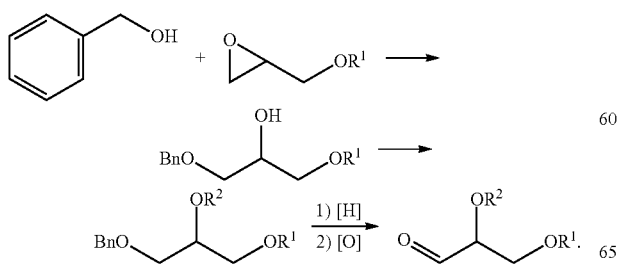

Further Embodiments

A compound for solubilizing a polymer having the formula:

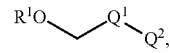

wherein $R^1$ is selected from: $C_{1-10}$ alkyl; $C_{6-18}$ aryl; $C_{3-10}$ cycloalkyl; $C_{1-10}$ heteroalkyl; $C_{6-18}$ heterocyclyl;

$Q^1$ represents a moiety having the structure:

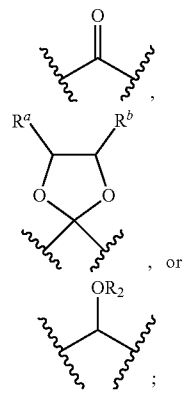

$Q^2$ represents a moiety having the structure:

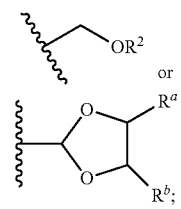

wherein $R^2$ is selected from: hydrogen; $C_{1-10}$ alkyl; $C_{6-18}$ aryl; $C_{3-10}$ cycloalkyl; $C_{1-10}$ heteroalkyl; $C_{6-18}$ heterocyclyl, one of $R^a$ and $R^b$ is hydrogen, and the other is —$CH_2OR^3$ wherein $R^3$ is selected from: hydrogen; $C_{1-10}$ alkyl; $C_{6-18}$ aryl; $C_{3-10}$ cycloalkyl; $C_{1-10}$ heteroalkyl; $C_{6-18}$ heterocyclyl, wherein the compound contains no more than one $R^2$ group, and no more than one $R^3$ group.

In some instances the compound has the formula:

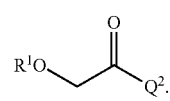

In some instances the compound has the formula:

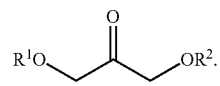

In some instances the compound has the formula:

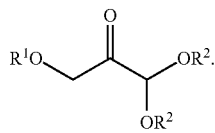

In some instances the compound has the formula:

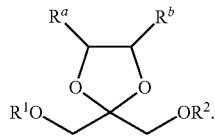

In some instances the compound has the formula:

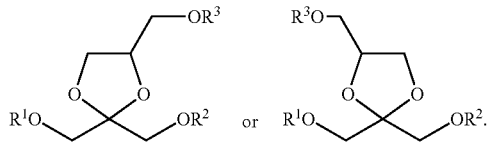

In some instances the compound has the formula:

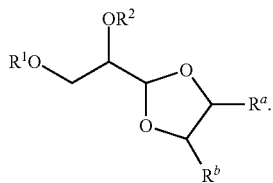

In some instances the compound has the formula:

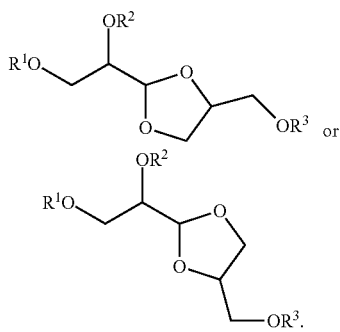

In some instances $R^1$ is $C_{1-10}$alkyl, optionally substituted one or more times by $R^{1a}$, $OR^{1a}$, $N(R^{1a})_2$, $SiR^{1a}{}_3$, $SR^{1a}$, $SO_2R^{1a}$, $SO_2N(R^{1a})_2$, $C(O)R^{1a}$; $C(O)OR^{1a}$, $OCOR^{1a}$; $C(O)N(R^{1a})_2$, $OC(O)N(R^{1a})_2$, $N(R^{1a})C(O)N(R^{1a})_2$, F, Cl, Br, I, cyano, and nitro, wherein $R^{1a}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl; wherein any two or more of $R^{1a}$ may together form a ring.

In some instances $R^1$ has the formula:

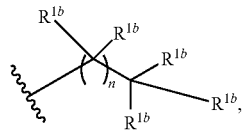

wherein n is selected from 0-9, and $R^{1b}$ is in each case independently selected from F, Cl, Br, I, cyano, nitro, $R^{1b'}$, and $OR^{1b'}$, wherein $R^{1b'}$ is in each case independently selected from hydrogen, $C_{1-10}$ alkyl; $C_{6-18}$aryl; $C_{3-10}$ cycloalkyl; $C_{1-10}$heteroalkyl; $C_{6-18}$ heterocyclyl; wherein any two or more of $R^{1b}$ may together form a ring.

In some instances n is 1.
In some instances n is 2.
In some instances n is 3.
In some instances n is 4.
In some instances n is 5.
In some instances n is 6.
In some instances n is 7.
In some instances n is 8.
In some instances n is 9.
In some instances $R^{1b}$ is in each case independently selected from hydrogen and F.

In some instances, $R^1$ has the formula:

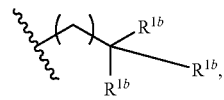

wherein n is 0-9, and $R^{1b}$ is independently selected from hydrogen and F.

In some instances n is 0, 1, or 2, and $R^{1b}$ is in each case F.

In some instances $R^1$ has the formula:

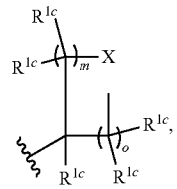

wherein m is from 0-9, o is from 0-9, wherein the sum of m+o does not exceed 9;

X is selected from O, S, $NR^{1c'}$; $R^{1C}$ is in each case independently selected from F, Cl, Br, I, $R^{1c'}$, $OR^{1c'}$, wherein $R^{1c'}$ is in each case independently selected from hydrogen, $C_{1-10}$alkyl; $C_{6-18}$ aryl; $C_{3-10}$ cycloalkyl; $C_{1-10}$heteroalkyl; $C_{6-18}$ heterocyclyl; wherein any two or more of $R^{1c}$ may together form a ring.

In some instances X is O.
In some instances m and o are both 2.
In some instances m is 1 and o is 2.
In some instances $R^{1c}$ is selected from hydrogen and F.
In some instances $R^{1c}$ is in each case hydrogen.

In some instances $R^1$ has the formula:

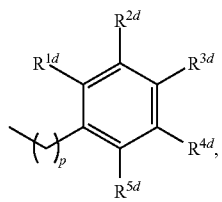

wherein p is selected from 0-9;
$R^{1d}$ is selected from hydrogen, F, Cl, Br, I, cyano, nitro, $R^{1d'}$, and $OR^{1d'}$, wherein $R^{1d'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
$R^{2d}$ is selected from hydrogen, F, Cl, Br, I, cyano, nitro, $R^{2d'}$, and $OR^{2d'}$, wherein $R^{2d'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
$R^{3d}$ is selected from hydrogen, F, Cl, Br, I, cyano, nitro, $R^{3d'}$, and $OR^{3d'}$, wherein $R^{3d'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl;
$R^{4d}$ is selected from hydrogen, F, Cl, Br, I, cyano, nitro, $R^{4d'}$, and $OR^{4d'}$, wherein $R^{4d'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
$R^{5d}$ is selected from hydrogen, F, Cl, Br, I, cyano, nitro, $R^{5d'}$, and $OR^{5d'}$, wherein $R^{5d'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
wherein any two or more of $R^{1d'}$, $R^{2d'}$, $R^{3d'}$, $R^{4d'}$, and $R^{5d'}$ may together form a ring.

In some instances p is 0 or 1.
In some instances $R^{1d}$ is selected from hydrogen, F, or $OR^{1d'}$, wherein $R^{1d'}$ is in each case independently selected from $C_{1-10}$ alkyl.
In some instances $R^{2d}$ is selected from hydrogen, F, or $OR^{2d'}$, wherein $R^{2d'}$ is in each case independently selected from $C_{1-10}$ alkyl.
In some instances $R^{3d}$ is selected from hydrogen, F, or $OR^{3d'}$, wherein $R^{3d'}$ is in each case independently selected from $C_{1-10}$alkyl.
In some instances $R^{4d}$ is selected from hydrogen, F, or $OR^{4d'}$, wherein $R^{4d'}$ is in each case independently selected from $C_{1-10}$ alkyl.
In some instances $R^{5d}$ is selected from hydrogen, F, or $OR^{5d'}$, wherein $R^{5d'}$ is in each case independently selected from $C_{1-10}$ alkyl.
In some instances $R^2$ is $C_{1-10}$alkyl, optionally substituted one or more times by $R^{2e}$, $OR^{2e}$, $N(R^{2e})_2$, $SiR^{2e}3$, $SR^{2er}$, $SO_2R^{2e}$, $SO_2N(R^{2e})_2$, $C(O)R^{2e}$; $C(O)OR^{2e}$, $OCOR^{2e}$; $C(O)N(R^{2e})_2$, $OC(O)N(R^{2e})_2$, $N(R^{2e})C(O)N(R^{2e})_2$, F, Cl, Br, I, cyano, and nitro, wherein $R^{2e}$ is in each case independently selected from hydrogen, $C_{1-10}$alkyl; $C_{6-18}$aryl; $C_{3-10}$ cycloalkyl; $C_{1-10}$heteroalkyl; $C_{6-18}$ heterocyclyl; wherein any two or more of $R^{2e}$ may together form a ring.
In some instances $R^1$ is a $C_{1-10}$alkyl group, a $C_{1-6}$alkyl group, or a $C_{1-4}$alkyl group, in each case optionally substituted one or more times by Cl, F, Br, I, $C_{6-18}$ aryl, $C_{1-10}$ alkoxy, or $C_{1-10}$ haloalkoxy.
In some instances $R^1$ is methyl, ethyl, n-propyl, isopropyl, n-butyl, isobutyl, tert-butyl, sec-butyl, trifluoromethyl, 2,2,2-trifluoroethyl, 2-methoxyethyl, 2-trifluoromethoxyethyl, benzyl, 4-fluorobenzyl, 4-trifluoromethylbenzyl, 4-methoxybenzyl, 2-fluorobenzyl, 2-trifluoromethylbenzyl, 2-methoxybenzyl, 3-fluorobenzyl, 3-trifluoromethylbenzyl, and 3-methoxybenzyl.

In some instances $R^2$ has the formula:

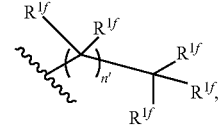

wherein n' is selected from 0-9, and $R^{1f}$ is in each case independently selected from F, Cl, Br, I, cyano, nitro, $R^{1'}$, and $OR^{1'}$, wherein $R^{1'}$ is in each case independently selected from hydrogen, $C_{1-10}$alkyl; $C_{6-18}$aryl; $C_{3-10}$ cycloalkyl; $C_{1-10}$heteroalkyl; $C_{6-18}$heterocyclyl; wherein any two or more of $R^{1f}$ may together form a ring.
In some instances n' is 1.
In some instances n' is 2.
In some instances n' is 3.
In some instances n' is 4.
In some instances n' is 5.
In some instances n' is 6.
In some instances n' is 7.
In some instances n' is 9.
In some instances $R^{1f}$ is in each case independently selected from hydrogen and F.
The compound according to an earlier embodiment, where $R^2$ has the formula:

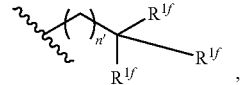

wherein n' is 0-9, and $R^{1f}$ is independently selected from hydrogen and F.
In some instances n' is 0, 1, or 2, and $R^{1f}$ is in each case F.
In some instances $R^2$ has the formula:

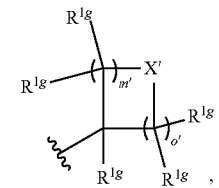

wherein m' is from 0-9, o' is from 0-9, wherein the sum of m'+o' does not exceed 9;
X' is selected from O, S, $NR^{1g'}$;
$R^{1g}$ is in each case independently selected from F, Cl, Br, I, $R^{1g'}$, $OR^{1g'}$, wherein $R^{19'}$ is in each case independently selected from hydrogen, $C_{1-10}$alkyl; $C_{6-18}$aryl; $C_{3-10}$ cycloalkyl; $C_{1-10}$ heteroalkyl;
$C_{6-18}$ heterocyclyl; wherein any two or more of $R^{1c}$ may together form a ring.
In some instances X' is O.
In some instances m' and o' are both 2.
In some instances m' is 1 and o' is 2.
In some instances $R^{1g}$ is selected from hydrogen and F.

In some instances $R^{1g}$ is in each case hydrogen.
In some instances $R^2$ has the formula:

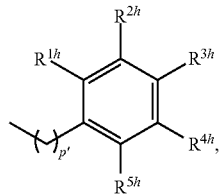

wherein p' is selected from 0-9;
$R^{1h}$ is selected from hydrogen, F, Cl, Br, I, cyano, nitro, $R^{1h'}$, and $OR^{1h'}$, wherein $R^{1h'}$ is in each case independently selected from hydrogen, $C_{1-10}$alkyl; $C_{6-18}$ aryl; $C_{3-10}$ cycloalkyl; $C_{1-10}$ heteroalkyl; $C_{6-18}$ heterocyclyl;
$R^{2h}$ is selected from hydrogen, F, Cl, Br, I, cyano, nitro, $R^{2h'}$, and $OR^{2h'}$, wherein $R^{2h'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
$R^{3h}$ is selected from hydrogen, F, Cl, Br, I, cyano, nitro, $R^{3h'}$, and $OR^{3h'}$, wherein $R^{3h'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl;
$R^{4h}$ is selected from hydrogen, F, Cl, Br, I, cyano, nitro, $R^{4h'}$, and $OR^{4h'}$, wherein $R^{4h'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
$R^{5h}$ is selected from hydrogen, F, Cl, Br, I, cyano, nitro, $R^{5h'}$, and $OR^{5h'}$, wherein $R^{5h'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl;
wherein any two or more of $R^{1h'}$, $R^{2h'}$, $R^{3h'}$, $R^{4h'}$, and $R^{5h'}$ may together form a ring.

In some instances p' is 0 or 1.
In some instances $R^{1h}$ is selected from hydrogen, F, or $OR^{h'}$, wherein $R^{1h'}$ is in each case independently selected from $C_{1-10}$ alkyl.
In some instances $R^{2h}$ is selected from hydrogen, F, or $OR^{2h'}$, wherein $R^{2h'}$ is in each case independently selected from $C_{1-10}$ alkyl.
In some instances $R^{3h}$ is selected from hydrogen, F, or $OR^{3h'}$, wherein $R^{3h'}$ is in each case independently selected from $C_{1-10}$ alkyl.
In some instances $R^{4h}$ is selected from hydrogen, F, or $OR^{4h'}$, wherein $R^{4h'}$ is in each case independently selected from $C_{1-10}$ alkyl.
In some instances $R^{5d}$ is selected from hydrogen, F, or $OR^{5h'}$, wherein $R^{5h'}$ is in each case independently selected from $C_{1-10}$ alkyl.
In some instances $R^2$ is hydrogen.
In some instances $R^3$ has the formula:

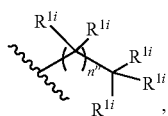

wherein n" is selected from 0-9, and $R^{1i}$ is in each case independently selected from F, Cl, Br, I, cyano, nitro, $R^{1i'}$, and $OR^{1i'}$, wherein $R^{1i'}$ is in each case independently selected from hydrogen, $C_{1-10}$alkyl; $C_{6-18}$aryl; $C_{3-10}$ cycloalkyl; $C_{1-10}$ heteroalkyl; $C_{6-18}$ heterocyclyl; wherein any two or more of $R^{1i'}$ may together form a ring.

In some instances n" is 1.
In some instances n" is 2.
In some instances n" is 3.
In some instances n" is 4.
In some instances n" is 5.
In some instances n" is 6.
In some instances n" is 7.
In some instances n" is 8.
In some instances n" is 9.
In some instances $R^{1i}$ is in each case independently selected from hydrogen and F.
The compound according to an earlier embodiment, where $R^3$ has the formula:

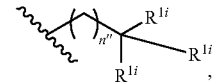

wherein n" is 0-9, and $R^{1i}$ is independently selected from hydrogen and F.
In some instances n" is 0, 1, or 2, and $R^{1i}$ is in each case F.
In some instances $R^3$ has the formula:

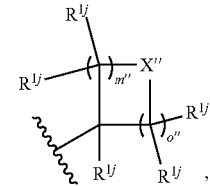

wherein m" is from 0-9, o" is from 0-9, wherein the sum of m"+o" does not exceed 9;
X" is selected from O, S, $NR^{1j'}$;
$R^{1j}$ is in each case independently selected from F, Cl, Br, I, $R^{1j'}$, $OR^{1j'}$, wherein $R^{1j'}$ is in each case independently selected from hydrogen, $C_{1-10}$alkyl; $C_{6-18}$ aryl; $C_{3-10}$ cycloalkyl; $C_{1-10}$ heteroalkyl; $C_{6-18}$ heterocyclyl; wherein any two or more of $R^{1j}$ may together form a ring.

In some instances X" is O.
In some instances m" and o" are both 2.
In some instances $R^{1j}$ is selected from hydrogen and F.
In some instances $R^{1j}$ is in each case hydrogen.
In some instances $R^3$ has the formula:

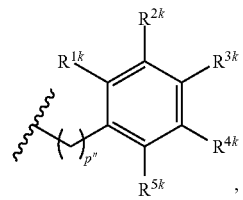

wherein p" is selected from 0-9;
$R^{1k}$ is selected from hydrogen, F, Cl, Br, I, cyano, nitro, $R^{1k'}$, and $OR^{k'}$, wherein $R^{1k'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl; $R^{2k}$ is selected from hydrogen, F, Cl, Br, I, cyano, nitro, $R^{2k'}$, and $OR^{2k'}$, wherein $R^{2k'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl; $R^{3k}$ is selected from hydrogen, F, Cl, Br, I, cyano, nitro, $R^{3k'}$, and $OR^{3k'}$, wherein $R^{3k'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl; $R^{4k}$ is selected from hydrogen, F, Cl, Br, I, cyano, nitro, $R^{4k'}$, and $OR^{4k'}$, wherein $R^{4k'}$ is in each case independently selected from hydrogen, $C_{1-10}$ alkyl; $C_{6-18}$aryl; $C_{3-10}$ cycloalkyl; $C_{1-10}$ heteroalkyl; $C_{6-18}$ heterocyclyl; $R^{5k}$ is selected from hydrogen, F, Cl, Br, I, cyano, nitro, $R^{5k'}$, and $OR^{5k'}$, wherein $R^{5k'}$ is in each case independently selected from hydrogen, $C_{1-10}$ alkyl; $C_{6-18}$ aryl; $C_{3-10}$ cycloalkyl; $C_{1-10}$ heteroalkyl; $C_{6-18}$ heterocyclyl; wherein any two or more of $R^{1k'}$, $R^{2k'}$, $R^{3k'}$, $R^{4k'}$, and $R^{5k'}$ may together form a ring.

In some instances p" is 0 or 1.

In some instances $R^{1k}$ is selected from hydrogen, F, or $OR^{1k'}$, wherein $R^{1k'}$ is in each case independently selected from $C_{1-10}$ alkyl.

In some instances $R^{2k}$ is selected from hydrogen, F, or $OR^{2k'}$, wherein $R^{2k'}$ is in each case independently selected from $C_{1-10}$ alkyl.

In some instances $R^{3k}$ is selected from hydrogen, F, or $OR^{3k'}$, wherein $R^{3k'}$ is in each case independently selected from $C_{1-10}$ alkyl.

In some instances $R^{4k}$ is selected from hydrogen, F, or $OR^{4k'}$, wherein $R^{4k'}$ is in each case independently selected from $C_{1-10}$ alkyl.

In some instances $R^{5d}$ is selected from hydrogen, F, or $OR^{5k'}$, wherein $R^{5k'}$ is in each case independently selected from $C_{1-10}$ alkyl.

In some instances $R^3$ is hydrogen.

In some instances $R^2$ is a $C_{1-10}$ alkyl group, a $C_{1-6}$alkyl group, or a $C_{1-4}$ alkyl group, in each case optionally substituted one or more times by Cl, F, Br, I, $C_{6-18}$aryl, $C_{1-10}$ alkoxy, or $C_{1-10}$ haloalkoxy.

In some instances $R^2$ is methyl, ethyl, n-propyl, isopropyl, n-butyl, isobutyl, tert-butyl, sec-butyl, trifluoromethyl, 2,2,2-trifluoroethyl, 2-methoxyethyl, 2-trifluoromethoxyethyl, benzyl, 4-fluorobenzyl, 4-trifluoromethylbenzyl, 4-methoxybenzyl, 2-fluorobenzyl, 2-trifluoromethylbenzyl, 2-methoxybenzyl, 3-fluorobenzyl, 3-trifluoromethylbenzyl, and 3-methoxybenzyl.

A method for dissolving a polymer, wherein the polymer comprises polyethylene, polypropylene, polyethylene terephthalate, polyvinylchloride, polystyrene; polyacrylonitrile, polychlorprene, polytetrafluoroethylene, polyamide, for example nylon, Kevlar, or Nomex, and mixtures thereof.

The method according to an earlier embodiment, wherein the polymer has a molecular weight from 2,500-100,000 Da, from 5,000-100,000 Da, from 7,500-100,000 Da, from 10,000-100,000 Da, from 2,500-50,000 Da, from 2,500-25,000 Da, from 5,000-25,000 Da, or from 5,000-15,000 Da.

The method according to an earlier embodiment, wherein the polymer has a molecular weight of at least 100,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, no greater than 600,000 Da, no greater than 500,000 Da, no greater than 400,000 Da, no greater than 300,000 Da, no greater than 200,000 Da.

98. The method according to an earlier embodiment, wherein the polymer has a molecular weight of at least 250,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, no greater than 600,000 Da, no greater than 500,000 Da, no greater than 400,000 Da, or no greater than 300,000 Da.

The method according to an earlier embodiment, wherein the polymer has a molecular weight of at least 500,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, no greater than 800,000 Da, no greater than 700,000 Da, or no greater than 600,000 Da.

The method according to an earlier embodiment, wherein the polymer has a molecular weight of at least 750,000 Da, and no greater than 10,000,000 Da, no greater than 7,500,000 Da, no greater than 5,000,000 Da, no greater than 2,500,000 Da, no greater than 2,000,000 Da, no greater than 1,500,000 Da, no greater than 1,000,000 Da, no greater than 900,000 Da, or no greater than 800,000 Da.

The method according to an earlier embodiment, wherein the polymer has a molecular weight of at least 1,000,000 Da, and no greater than 10,000,000 Da, no greater than 7,500,000 Da, no greater than 5,000,000 Da, no greater than 2,500,000 Da, no greater than 2,000,000 Da, or no greater than 1,500,000 Da.

EXAMPLES

The following examples are for the purpose of illustration of the invention only and are not intended to limit the scope of the present invention in any manner whatsoever.

Example 1:
1,3-bis(2,2,2-trifluoroethoxy)propan-2-one
(DTEPK), [K,F,K]

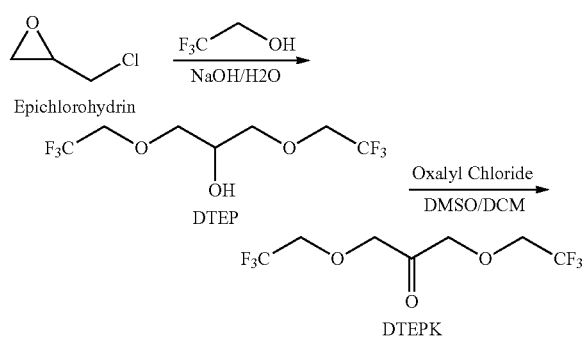

Synthesis of DTEP

Epichlorohydrin (46.26 g, 0.50 mol) was added dropwise to 2,2,2-trifluoroethanol (91.32 g, 1.20 mol) dissolved in 4 M aq. NaOH (300 mL) in a 1000 mL round bottom flask in 30 min at room temperature. The system was then heated to 80° C. and the reaction was running overnight before cooling down to room temperature. The reaction mixture was transferred into a 1000 mL separation funnel and the bottom organic layer was collected. $CH_2Cl_2$ (3×100 mL) was used to wash upper aqueous layer. The organic layers were combined, washed with 3×50 mL deionized $H_2O$ and dried over anhydrous $MgSO_4$. The solid was filtered and the solvent was removed through rotary evaporation under reduced pressure. The product was then distilled and stored over molecular sieves. Isolated yield of DTEP is 92.37 g (72.1%) [1].

Synthesis of DTEPK

Oxalyl chloride (~20 mL, 0.22 mol) dissolved in 150 mL DCM was put in a 1000 mL round bottom flask and was cooled down to −60° C. in dry ice/acetone bath. DMSO (~34 mL, 0.32 mol) dissolved in 50 mL $CH_2Cl_2$ was added dropwise in 5 min and stirred for another 10 min. DTEP (51.23 g, 0.2 mol) dissolved in 60 mL $CH_2Cl_2$ was then added dropwise in 5 min and stirred for another 15 min. Triethylamine (140 mL) was then added in 5 min and the cooling bath was removed to let reaction system back to room temperature. DI water (120 mL) was added and stirred for 10 min before being transferred into a 1000 mL separation funnel. $CH_2Cl_2$ (200 mL) was added to extract organic compounds. The bottom layer was collected after separation, washed with brine (3×50 mL), dried over anhydrous $MgSO_4$, filtered and the solvent was removed via rotary evaporation under reduced pressure. The product was then distilled and stored over molecular sieves. Isolated yield of DTEPK is 40.25 g (79.2%). $^1H$ NMR (500 MHz, DMSO-$d_6$) δ 4.44 (d, J=1.3 Hz, 4H), 4.14 (d, J=9.3 Hz, 4H).

Example 2: 1-(2-methoxyethoxy)-3-(2,2,2-trifluoroethoxy)propan-2-one (AMTEPK)

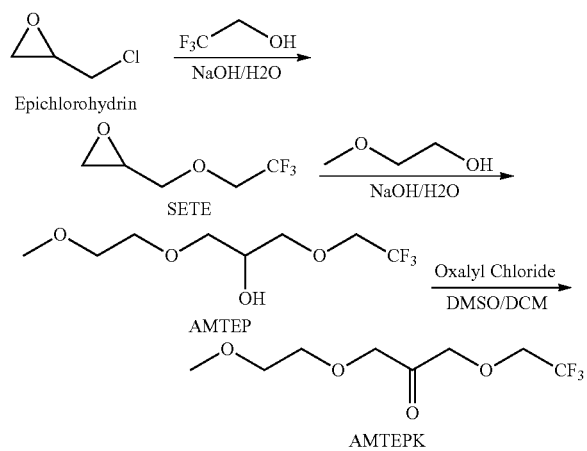

Synthesis of SETE 2,2,2-trifluoroethanol (260.1 g, 2.6 mol) dissolved in 5.5 M aq. NaOH (400 mL) was added dropwise to epichlorohydrin (185.1 g, 2 mol) in 1 h in a 2000 mL round bottom flask in ice bath. After that, the ice bath was removed and reaction mixture was kept stirring for 60 h at room temperature before being transferred into a 1000 mL separation funnel. The bottom layer was collected, the upper layer was extracted with diethyl ether (3×200 mL). The organic phase was combined and washed with brine (3×80 mL), dried over anhydrous $MgSO_4$. The solid was then filtered off and solvent was removed via rotary evaporation under reduced pressure. The product was then distilled and stored over molecular sieves. Isolated yield of SETE is 233.89 g (74.9%).

Synthesis of AMTEP

To a 1000 mL round bottom flask with NaOH (32 g, 0.8 mol) powder was added 2-methoxyethanol (95 mL, 1.2 mol), the mixture was heated to 50° C. while stirring for 20 min before addition of SETE (124.88 g, 0.8 mol). The reaction was running overnight before quenched by 50 mL DI water. The mixture was then filtered and product was extracted by diethyl ether (3×150 mL). The organic phase was then washed with brine (3×50 mL), dried over anhydrous $MgSO_4$, filtered and solvent was removed via rotary evaporation under reduced pressure. The product was then distilled and stored over molecular sieves. Isolated yield of AMTEP is 111.69 g (60.1%).

Synthesis of AMTEPK

Oxalyl chloride (~30 mL, 0.33 mol) dissolved in 200 mL DCM was put in a 1000 mL round bottom flask and was cooled down to −60° C. via dry ice/acetone. DMSO (~51 mL, 0.32 mol) dissolved in 70 mL $CH_2Cl_2$ was added dropwise in 5 min and stirred for another 10 min. AMTEP (69.66 g, 0.3 mol) dissolved in 100 mL $CH_2Cl_2$ was then added dropwise in 5 min and stirred for another 15 min. Triethylamine (210 mL) was then added in 5 min and the cooling bath was removed to let reaction system back to room temperature. DI water (150 mL) was added and stirred for 10 min before being transferred into a 1000 mL separation funnel. $CH_2Cl_2$ (300 mL) was added to extract organic compounds. The bottom layer was collected after separation, washed with brine (3×50 mL), dried over anhydrous $MgSO_4$, filtered and the solvent was removed via rotary evaporation under reduced pressure. The product was then distilled and stored over molecular sieves. Isolated yield of AMTEPK is 54.59 g (79.1%). $^1H$ NMR (500 MHz, DMSO-$d_6$) δ 4.47 (s, 2H), 4.20 (s, 2H), 4.12 (q, J=9.2 Hz, 2H), 3.61-3.56 (m, 2H), 3.49-3.45 (m, 2H), 3.26 (d, J=1.2 Hz, 3H).

Example 3: 2.2.1.1 1,3-diethoxypropan-2-ol ([E, 0, E])

To a 1000 mL round bottom flask loaded with 500 mL EtOH at RT was added sodium metal ($Na^0$ (25.3 g, 1.10 mol). Temperature was raised to 70° C. upon depletion of $Na^0$, followed by addition of epichlorohydrin (46.7 g, 0.50 mol) dropwise. Reaction was kept overnight at 70° C. before the excess EtOH was removed by rotary evaporation under reduced pressure. 400 mL $Et_2O$ was then added to the crude product and the precipitate was removed by filtration. The solution was then neutralized with 1 M HCl. The mixture was transferred into a 1000 mL separation funnel, where the $Et_2O$ phase was collected and the aqueous phase was further washed with 3×100 mL $Et_2O$. The organic phases were combined and dried over anhydrous $MgSO_4$. The solids were filtered and solvent was removed by rotary evaporation, followed by vacuum distillation to afford 54.67 g (73.8%) of [E, 0, E] as a clear, colorless liquid. $^1H$ NMR (500 MHz, DMSO-$d_6$) δ 4.71 (d, J=5.2 Hz, 1H), 3.69 (qd, J=5.8, 5.0 Hz, 1H), 3.47-3.39 (m, 4H), 3.33 (dd, J=9.9, 5.1

Hz, 2H), 3.27 (dd, J=9.7, 6.0 Hz, 2H), 1.10 (td, J=7.0, 0.7 Hz, 6H). 1,3-bis(2-methoxyethoxy)propan-2-ol ([ME, 0, ME])

To a 1000 mL round bottom flask loaded with 600 mL 2-methoxyethanol (CH$_3$OCH$_2$CH$_2$OH) at RT was added Na$^0$ (75.9 g, 3.30 mol). The reaction temperature was raised to 80° C. upon depletion of Na$^0$, followed by dropwise addition of epichlorohydrin (140.2 g, 1.50 mol). The reaction was stirred overnight at 80° C. before cooling down to RT. The excess of CH$_3$OCH$_2$CH$_2$OH was removed by rotary evaporation under reduced pressure. 600 mL Et$_2$O was then added to the crude product and the precipitate was removed by filtration. The solution was then neutralized with 1 M HCl. The solids were filtered and Et$_2$O was then removed by rotary evaporation under reduced pressure, followed by vacuum distillation to afford 196.69 g (63.0%) [ME, 0, ME] as a clear, colorless liquid. $^1$H NMR (500 MHz, DMSO-d$_6$) δ 4.74 (d, J=5.2 Hz, 1H), 3.69 (dp, J=10.9, 5.2 Hz, 1H), 3.54-3.49 (m, 4H), 3.46-3.41 (m, 4H), 3.38 (dd, J=9.9, 5.0 Hz, 2H), 3.32 (dd, J=10.0, 5.9 Hz, 2H), 3.25 (s, 6H). 1,3-bis(2,2,2-trifluoroethoxy)propan-2-ol ([F, 0, F])

To a 1000 mL round bottom flask loaded with 4 M aq. NaOH (300 mL) at RT was added 2,2,2-trifluoroethanol (CF$_3$CH$_2$OH, 121.3 g, 1.20 mol) and stirred for 30 min before dropwise addition of epichlorohydrin (46.7 g, 0.50 mol). The reaction system was heated at 80° C. overnight before cooling to RT. The reaction mixture was then transferred to a 1000 mL separation funnel and the bottom organic layer was collected. The aqueous layer was washed with 3×100 mL CH$_2$Cl$_2$. The organic phases were combined, washed with 3×50 mL saturated NaHCO$_3$ solution, dried over anhydrous MgSO$_4$ and filtered. The solvent was removed by rotary evaporation under reduced pressure and the remaining product was further purified by vacuum distillation to afford 97.0 g (75.7%) [F, 0, F] as a clear, colorless liquid. $^1$H NMR (360 MHz, DMSO-d$_6$) δ 5.16 (d, J=5.2 Hz, 1H), 4.10 (d, J=9.4 Hz, 2H), 4.05 (d, J=9.4 Hz, 2H), 3.80 (h, J=5.3 Hz, 1H), 3.58 (d, J=10.2, 5.3 Hz, 4H).

Example 4: 1,3-diethoxypropan-2-one ([E, K, E])

To a 1000 mL round bottom flask loaded with 260 mL CH$_2$Cl$_2$ at RT was added oxalyl chloride (40 mL, 0.44 mol). The flask was then placed in a dry ice-acetone cooling bath (−78° C.). DMSO (68 mL, 0.64 mol) mixed with 80 mL CH$_2$Cl$_2$ was added slowly over 10 min and maintained for another 10 min until no further gas evolved from the reaction system. Then addition of [E, 0, E] (59.3 g, 0.40 mol) dissolved in 100 mL CH$_2$Cl$_2$ occurred over 10 min. The reaction was maintained for another 20 min before quenching with Et$_3$N (278 mL, 2.00 mol). The cooling bath was removed after 1 h to allow the reaction system to warm to ambient temperature, after which 130 mL deionized water was added. After stirring for 30 min in the presence of water, the mixture was transferred to a 1000 mL separation funnel. The bottom CH$_2$Cl$_2$ layer was collected and the aqueous layer was washed with 3×100 mL CH$_2$Cl$_2$. The organic layers were combined, washed with 3×50 mL saturated NaHCO$_3$ water solution, dried over anhydrous MgSO$_4$ and filtered, followed by removal of CH$_2$Cl$_2$ by rotary evaporation under reduced pressure. The remaining product was further purified by vacuum distillation to afford 45.22 g (77.3%) [E, K, E] as a clear, colorless liquid. $^1$H NMR (500 MHz, DMSO-d$_6$) δ 4.16 (s, 4H), 3.46 (q, J=7.0 Hz, 4H), 1.12 (t, J=7.0 Hz, 6H).

Example 5: 2,5,9,12-tetraoxatridecan-7-one ([ME, K, ME])

To a 1000 mL round bottom flask loaded with 200 mL CH$_2$Cl$_2$ at RT was added oxalyl chloride (30 mL, 0.33 mol). The flask was then placed in a dry ice-acetone cooling bath. DMSO (52 mL, 0.48 mol) mixed with 70 mL CH$_2$Cl$_2$ was added slowly over 10 min and maintained for another 10 min until no further gas evolved from the reaction system. Then, addition of [ME, 0, ME] (62.5 g, 0.30 mol) dissolved in 100 mL CH$_2$Cl$_2$ occurred over 10 min. The reaction was kept for another 20 min before being quenched by Et$_3$N (209 mL, 1.50 mol). The cooling bath was removed after 1 h to allow the reaction system to warm to ambient temperature, after which 100 mL deionized water was added. After stirring for 30 min in the presence of water, the mixture was transferred into a 1000 mL separation funnel. Then the upper aqueous layer was collected and the CH$_2$Cl$_2$ layer was washed with 3×50 mL deionized water. The aqueous layers were combined, washed with 3×50 mL Et$_2$O, followed by removal of water by rotary evaporation under reduced pressure. 300 mL Et$_2$O was added to the remaining mixture, the precipitate was filtered and Et$_2$O was removed by rotary evaporation. The remaining product was further purified by vacuum distillation to afford 30.30 g (49.0%) [ME, K, ME] as a clear, colorless liquid. $^1$H NMR (500 MHz, DMSO-d$_6$) δ 4.21 (s, 4H), 3.58-3.54 (m, 4H), 3.47-3.43 (m, 4H), 3.25 (s, 6H).

Example 6: 1,3-bis(2,2,2-trifluoroethoxy)propan-2-one ([F, K, F])

To a 1000 mL round bottom flask loaded with 150 mL CH$_2$Cl$_2$ at RT was added oxalyl chloride (20 mL, 0.22 mol). The flask was then placed in a dry ice-acetone cooling bath. DMSO (34 mL, 0.32 mol) mixed with 50 mL CH$_2$Cl$_2$ was added slowly over 5 min and maintained for another 10 min until no further gas evolved from the reaction. Then, addition of [F, 0, F] (51.2 g, 0.20 mol) dissolved in 60 mL CH$_2$Cl$_2$ occurred over 5 min. The reaction was maintained for another 15 min before quenching with Et$_3$N (140 mL, 1.0 mol). The cooling bath was removed after 1 h to allow the reaction to warm back to ambient temperature, after which 120 mL deionized water was added. After stirring for 10 min in the presence of water, the mixture was transferred into a 1000 mL separation funnel. Then the bottom CH$_2$Cl$_2$ layer was collected and the aqueous layer was washed with 3×100 mL CH$_2$Cl$_2$. The organic layers were combined, washed with 3×50 mL saturated NaHCO$_3$ water solution, dried over anhydrous MgSO$_4$ and filtered, followed by removal of CH$_2$Cl$_2$ by rotary evaporation under reduced pressure. The remaining product was further purified by vacuum distillation to afford 40.25 g (79.2%) [F, K, F] as a clear, colorless liquid. $^1$H NMR (500 MHz, DMSO-d$_6$) δ 4.44 (s, 4H), 4.14 (q, J=9.3 Hz, 4H).

Example 7: 7-(2-methoxyethoxy)-2,5,9,12-tetraoxatridecane ([ME, ME, ME])

To a 250 mL round bottom flask loaded with 100 mL DMSO at RT was added [ME, 0, ME] (62.5 g, 0.30 mol) and NaOH powder (24.7 g, 0.60 mol). The mixture was stirred for 30 min, followed by addition of 2-Chloroethyl methyl ether (CH$_3$OCH$_2$CH$_2$Cl, 57.8 g, 0.60 mol). The temperature was then raised to 50° C. and the reaction stirred at this temperature overnight (~16 h). Upon cooling to RT, the mixture was filtered to remove the solid byproduct. The product was then extracted from DMSO with 3×200 mL Et$_2$O. The ether phase was dried with anhydrous MgSO$_4$ and filtered, followed by solvent removal by rotary evaporation. The remaining product was further purified by vacuum distillation to afford 42.0 g (52.6%) [ME, ME, ME] as a clear, colorless liquid. $^1$H NMR (500 MHz, DMSO-d$_6$) δ 3.65-3.60 (m, 2H), 3.55-3.50 (m, 5H), 3.47-3.38 (m, 10H), 3.24 (d, J=3.5 Hz, 9H).

Example 8: 2-(2-methoxyethoxy)-1,3-bis(2,2,2-trifluoroethoxy)propane ([F, ME, F])

To a 250 mL round bottom flask loaded with 100 mL DMSO at RT was added [F, 0, F](64.0 g, 0.25 mol) and NaOH powder (20.6 g, 0.50 mol). The mixture was stirred for 30 min, followed by addition of 2-Chloroethyl methyl ether (CH$_3$OCH$_2$CH$_2$Cl, 48.2 g, 0.50 mol). The temperature was then raised to 50° C. and the reaction stirred at this temperature overnight (~16 h). Upon cooling to RT, the mixture was filtered first to remove the solid byproduct. The liquid filtrate was poured into 100 mL deionized water. The aqueous phase was then extracted with 3×200 mL Et$_2$O. The organic layers were combined and then washed with 3×50 mL deionized water, dried over anhydrous MgSO$_4$ and filtered. The solvent was removed by rotary evaporation and the remaining was distilled to afford 69.04 g (87.9%) [F, ME, F] as a clear, colorless liquid. $^1$H NMR (500 MHz, DMSO-d$_6$) δ 4.08 (qd, J=9.4, 1.1 Hz, 4H), 3.72-3.59 (m, 7H), 3.46-3.41 (m, 2H), 3.25 (s, 3H).

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

The invention claimed is:

1. A compound of Formula (I):

[Formula (I)]

wherein R$^1$ is selected from: C$_{1-10}$alkyl; C$_{6-18}$aryl; C$_{3-10}$cycloalkyl; C$_{1-10}$heteroalkyl; C$_{6-18}$heterocyclyl; optionally substituted one or more times by Cl, F, Br, I, C$_{6-18}$aryl, C$_1$-C$_{10}$alkoxy, or C$_{1-10}$haloalkoxy Q$^1$ represents a moiety having the structure:

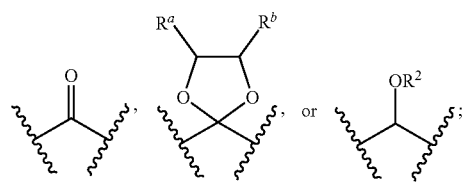

Q$^2$ represents a moiety having the structure:

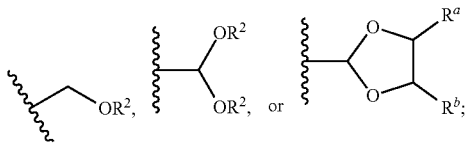

wherein R$^2$ is selected from: hydrogen; C$_{1-10}$alkyl; C$_{6-18}$aryl; C$_{3-10}$cycloalkyl; C$_{1-10}$heteroalkyl; C$_{6-18}$heterocyclyl, optionally substituted one or more times by Cl, F, Br, I, C$_{6-18}$aryl, C$_{1-10}$alkoxy, or C$_{1-10}$haloalkoxy one of R$^a$ and R$^b$ is hydrogen, and the other is -CH$_2$OR$^3$ wherein R$^3$ is selected from: hydrogen; C$_{1-10}$alkyl; C$_{6-18}$aryl; C$_{3-10}$cycloalkyl; C$_{1-10}$heteroalkyl; C$_{6-18}$heterocyclyl, wherein Q$^1$ and Q$^2$ do not both include an R$^2$ group; and also wherein Q$^1$ and Q$^2$ do not both include an R$^3$ group;

wherein R$^1$ and R$^2$ are not the same; and wherein neither R$^1$ nor R$^2$ are isopropyl, tert-butyl, n-butyl, or p-methoxybenzyl.

2. The compound of claim 1, wherein R$^1$ is a C$_{1-4}$alkyl group optionally substituted one or more times by Cl, F, Br, I, C$_{6-18}$aryl, C$_{1-10}$alkoxy, or C$_{1-10}$haloalkoxy.

3. The compound of claim 2, wherein R$^1$ is a C$_{1-4}$alkyl group substituted by a C$_{1-10}$alkoxy group.

4. The compound of claim 2, wherein R$^1$ is 2-methoxyethyl.

5. The compound of claim 3, wherein R$^1$ is a C$_{1-4}$alkyl group, substituted one or more times by F.

6. The compound of claim 5, wherein R$^1$ is trifluoromethyl, 2,2,2-trifluoroethyl, 2,2,3,3,3-pentafluoropropyl, or hexafluoroisopropyl.

7. The compound of claim 1, wherein Q$^2$ is:

and $R^2$ is a $C_{1-4}$alkyl group optionally substituted one or more times by Cl, F, Br, I, $C_{6-18}$aryl, $C_{1-10}$alkoxy, or $C_{1-10}$ haloalkoxy.

8. The compound of claim 7, wherein $R^2$ is a $C_{1-4}$alkyl group substituted by a $C_{1-10}$alkoxy group.

9. The compound of claim 8, wherein $R^2$ is 2-methoxyethyl.

10. The compound of claim 7, wherein $R^2$ is a $C_{1-4}$alkyl group, substituted one or more times by F.

11. The compound of claim 10, wherein $R^2$ is trifluoromethyl, 2,2,2-trifluoroethyl, 2,2,3,3,3-pentafluoropropyl, or hexafluoroisopropyl.

12. The compound of claim 1, wherein $Q^1$ represents a moiety having the structure:

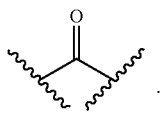

13. The compound of claim 1, wherein $Q^1$ represents a moiety having the structure:

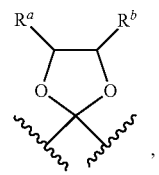

one of $R^a$ and $R^b$ is hydrogen, and the other is -$CH_2OR^3$, wherein $R^3$ has the formula:

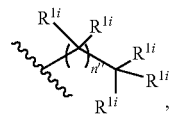

$R^{1i}$ is in each case independently selected from F, H, and $OR^{1i'}$, wherein $R^{1i'}$ is in each case independently selected from $C_{1-10}$alkyl; and n" is 0, 1, or 2.

14. A compound having the formula:

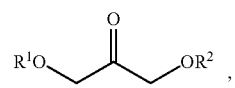

wherein $R^1$ is selected from trifluoromethyl, 2,2,2-trifluoroethyl, 2,2,3,3,3-pentafluoropropyl, hexafluoroisopropyl, 2-methoxyethyl, 2-trifluoromethoxyethyl, benzyl, 4-fluorobenzyl, 4-trifluoromethylbenzyl, 2-fluorobenzyl, 2-trifluoromethylbenzyl, 2-methoxybenzyl, 3-fluorobenzyl, 3-trifluoromethylbenzyl, and 3-methoxybenzyl; and $R^2$ is selected from trifluoromethyl, 2,2,2-trifluoroethyl, 2,2,3,3,3-pentafluoropropyl, hexafluoroisopropyl, 2-methoxyethyl, 2-trifluoromethoxyethyl, benzyl, 4-fluorobenzyl, 4-trifluoromethylbenzyl, 2-fluorobenzyl, 2-trifluoromethylbenzyl, 2-methoxybenzyl, 3-fluorobenzyl, 3-trifluoromethylbenzyl, and 3-methoxybenzyl.

15. A method for solubilizing a polymer, comprising contacting a polymer with a compound according to claim 1.

16. The method according to claim 15, wherein the polymer comprises polyethylene, polypropylene, polyethylene terephthalate, polyvinylchloride, polystyrene; polyacrylonitrile, polychloroprene, polytetrafluoroethylene, polyamide, or a mixture thereof.

* * * * *